(12) United States Patent
You et al.

(10) Patent No.: US 12,042,362 B2
(45) Date of Patent: Jul. 23, 2024

(54) METHOD OF MAKING AN ABSORBENT ARTICLE HAVING STRETCHABLE PANELS

(71) Applicant: Kimberly-Clark Worldwide, Inc., Neenah, WI (US)

(72) Inventors: KueYoung You, Youngin-Si (KR); Sarah A. O'Brien, Neenah, WI (US); MinJae Lee, Yongin-Si (KR); Seul Lee, Seongnam-si (KR); Jiyoung Haley Jung, Seongnam-si (KR); DaeGun Kim, Yongin-si (KR); Catherine M. Hancock-Cooke, Neenah, WI (US)

(73) Assignee: Kimberly-Clark Worldwide, Inc., Appleton, WI (US)

( * ) Notice: Subject to any disclaimer, the term of this patent is extended or adjusted under 35 U.S.C. 154(b) by 526 days.

(21) Appl. No.: 17/399,379

(22) Filed: Aug. 11, 2021

(65) Prior Publication Data

US 2021/0369505 A1  Dec. 2, 2021

Related U.S. Application Data

(62) Division of application No. 15/540,214, filed as application No. PCT/US2014/073022 on Dec. 31, 2014, now Pat. No. 11,116,674.

(51) Int. Cl.
*A61F 13/15*  (2006.01)
*A61F 13/496*  (2006.01)

(52) U.S. Cl.
CPC .. *A61F 13/15699* (2013.01); *A61F 13/15739* (2013.01); *A61F 13/15804* (2013.01); *A61F 13/496* (2013.01); *A61F 13/4963* (2013.01)

(58) Field of Classification Search
None
See application file for complete search history.

(56) References Cited

U.S. PATENT DOCUMENTS

| | | | |
|---|---|---|---|
| 2,435,945 A | 2/1948 | Redmond |
| 4,205,679 A | 6/1980 | Repke et al. |
| 4,701,171 A | 10/1987 | Boland et al. |
| 4,906,243 A | 3/1990 | Dravland |
| 4,940,464 A | 7/1990 | Van Gompel et al. |
| 5,182,815 A | 2/1993 | Young |

(Continued)

FOREIGN PATENT DOCUMENTS

| | | | |
|---|---|---|---|
| CN | 1607931 A | 4/2005 |
| CN | 1933795 A | 3/2007 |

(Continued)

*Primary Examiner* — Barbara J Musser
(74) *Attorney, Agent, or Firm* — KIMBERLY-CLARK WORLDWIDE, INC.

(57) ABSTRACT

An absorbent article includes bond seams that are positioned forwardly towards the article central longitudinal direction from the lateral-most side edges of the article, and which are aligned with the highest point of high-rise leg openings on the article. The absorbent article is conformable on both front and back panels, with the front panel being narrower in dimension than the back panel. The bond seams and leg openings can be seen on the front surface of the relaxed and flattened absorbent article. Such absorbent article may be manufactured along the article transverse direction by use of differential tension during manufacture, or differential retractive properties of elastic base materials.

6 Claims, 7 Drawing Sheets

(56) References Cited

U.S. PATENT DOCUMENTS

| | | | |
|---|---|---|---|
| 5,340,424 | A | 8/1994 | Matsushita |
| 5,411,498 | A | 5/1995 | Fahrenkrug et al. |
| 5,440,764 | A | 8/1995 | Matsushita |
| 5,643,396 | A | 7/1997 | Rajala et al. |
| 5,772,825 | A | 6/1998 | Schmitz |
| 6,240,569 | B1 | 6/2001 | Van Gompel et al. |
| 6,375,646 | B1 | 4/2002 | Widlund et al. |
| 6,478,785 | B1 | 11/2002 | Ashton et al. |
| 6,503,235 | B2 | 1/2003 | Suzuki et al. |
| 7,011,653 | B2 | 3/2006 | Imsangjan et al. |
| 7,066,921 | B2 | 6/2006 | Schmoker et al. |
| 7,344,524 | B2 | 3/2008 | Cazzato et al. |
| 7,419,562 | B2 | 9/2008 | Van Gompel et al. |
| 7,604,624 | B2 | 10/2009 | Veith et al. |
| 8,043,274 | B2 * | 10/2011 | Mlinar ............ A61F 13/4902 604/385.24 |
| 8,147,476 | B2 | 4/2012 | Veith et al. |
| 8,246,598 | B2 | 8/2012 | Vogt et al. |
| 8,361,046 | B2 * | 1/2013 | Bishop ............ A61F 13/49009 604/385.01 |
| 2002/0112276 | A1 | 8/2002 | Ruman et al. |
| 2003/0120240 | A1 | 6/2003 | Buell et al. |
| 2003/0168159 | A1 | 9/2003 | Een et al. |
| 2003/0229327 | A1 | 12/2003 | Imsangjan et al. |
| 2004/0127868 | A1 | 7/2004 | Olson et al. |
| 2007/0038199 | A1 | 2/2007 | Erdman et al. |
| 2007/0208317 | A1 | 9/2007 | Krautkramer et al. |
| 2008/0134487 | A1 | 6/2008 | Hartono |
| 2010/0168705 | A1 | 7/2010 | Stabelfeldt et al. |
| 2011/0098668 | A1 | 4/2011 | Thorson et al. |
| 2011/0125122 | A1 | 5/2011 | Thorson et al. |
| 2011/0313380 | A1 | 12/2011 | Ashton et al. |
| 2012/0253310 | A1 | 10/2012 | Hahn et al. |
| 2013/0138072 | A1 | 5/2013 | Morimoto et al. |
| 2014/0187405 | A1 | 7/2014 | Volp et al. |

FOREIGN PATENT DOCUMENTS

| | | |
|---|---|---|
| CN | 101820840 A | 9/2010 |
| CN | 102202629 A | 9/2011 |
| EP | 0878180 A2 | 11/1998 |
| GB | 2165457 A | 4/1986 |
| WO | 0037016 A1 | 6/2000 |
| WO | 2003075814 A1 | 9/2003 |
| WO | 2013164667 A1 | 11/2013 |
| WO | 2014050014 A1 | 4/2014 |

* cited by examiner

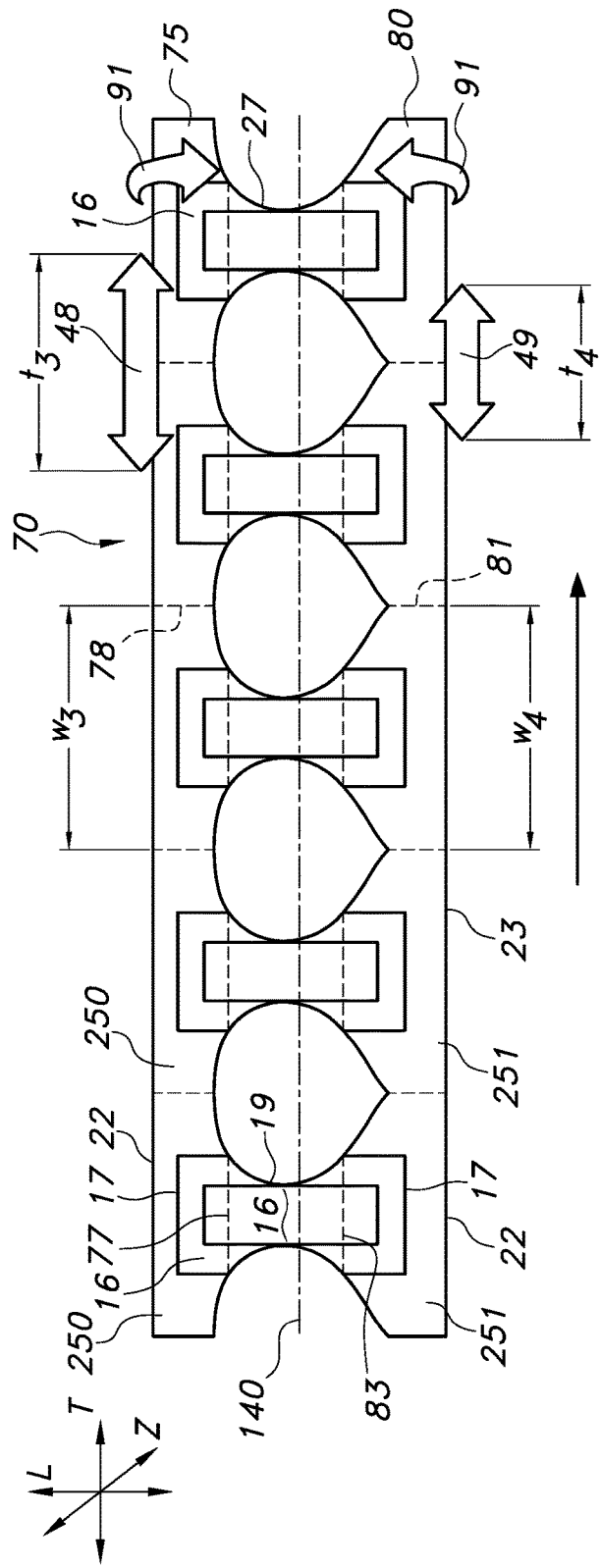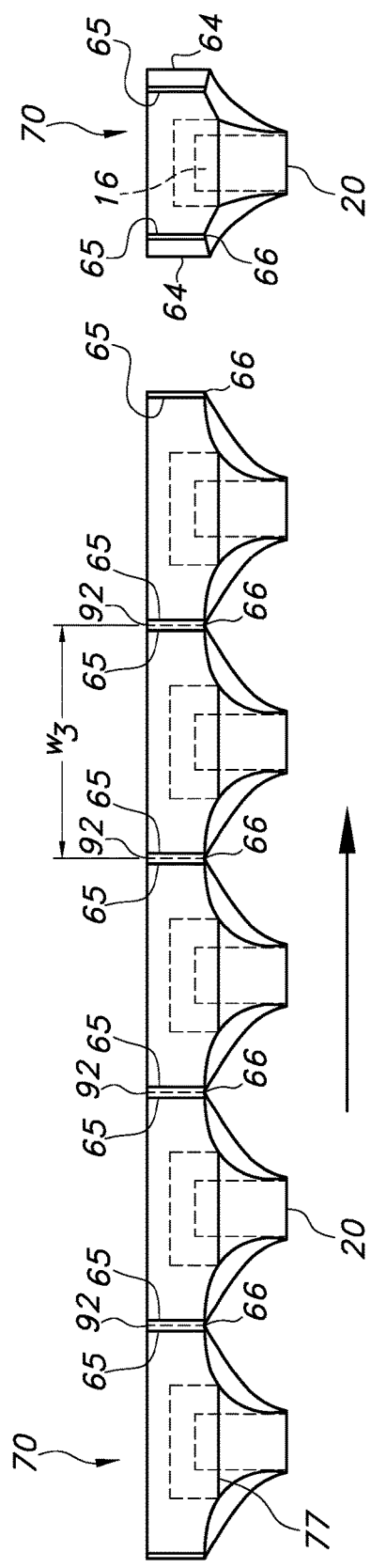
FIG. 4A
FIG. 4B

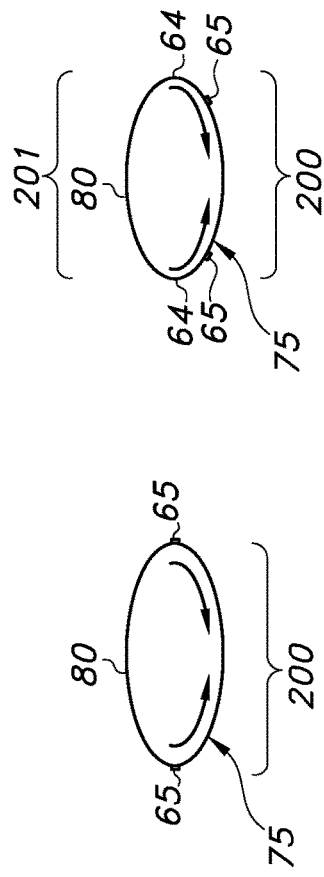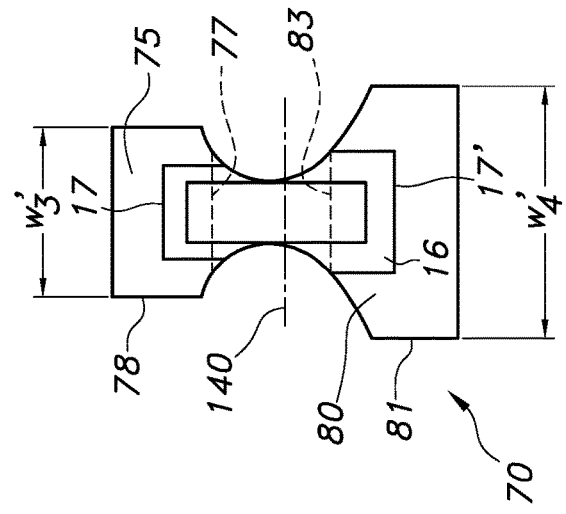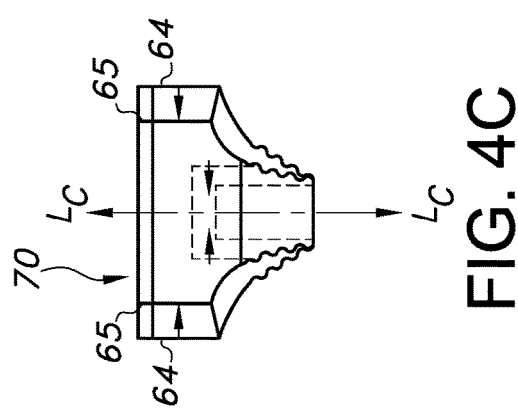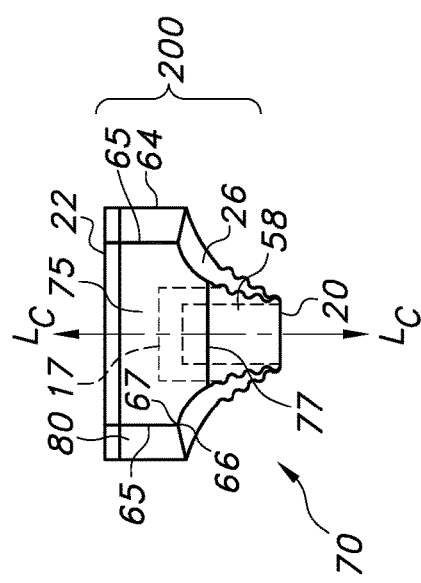

METHOD OF MAKING AN ABSORBENT ARTICLE HAVING STRETCHABLE PANELS

RELATED APPLICATIONS

The present application is a divisional application and claims priority to U.S. patent application Ser. No. 15/540,214, filed on Jun. 27, 2017, now U.S. Pat. No. 11,116,674 which is a national-phase entry, under 35 U.S.C. § 371, of PCT Patent Application No. PCT/US14/73022, filed on Dec. 31, 2014, all of which are incorporated herein by reference.

FIELD OF THE INVENTION

The present invention is generally directed to absorbent personal care articles to be worn around a user's lower abdominal region. In particular, the present invention is directed to absorbent garment-style, personal care articles such as absorbent briefs, pants, panties, and diapers with stretchable or extensible panels, as well as methods for producing such articles.

BACKGROUND OF THE INVENTION

Child care, feminine care, and adult hygiene-related absorbent personal care articles are often used to protect consumer outer garments from soiling, and to collect and retain body exudates such as menses, blood, feces, or urine. Such articles are often presented in disposable garment-like product formats (as opposed to inserts, pads, or liners), which garment-like articles serve as undergarments in place of traditional underwear. They are most commonly placed on a user by either being pulled up about a user's legs towards the user's lower abdomen, and placed adjacent a user's crotch region during use. Alternatively, such garment-like articles are refastenable, and therefore first placed between a user's legs at the crotch region, and fastened together at the article side edges around the user's lower abdomen, typically by adhesive, "hook-and-loop" type fasteners or a combination of the two.

Today, many users of absorbent, garment-like articles include adults who experience various forms of incontinence. Such adult consumers (as well as older children) are interested in the ability of an absorbent garment to both demonstrate sufficient liquid-holding capacity and fit, as well as a resemblance to traditional woven underwear. Such adult consumers are interested in product appearance, as there is a desire to enhance the overall personal experience of using such products, while reducing incontinence-related stigmas. Furthermore, older children who may benefit from wearing such absorbent articles are interested in articles that closely resemble the underwear of their peers. "Absorbent article" stigmas are aggravated by product designs which are seen as bulky and ill-fitting; by product designs having an outline that can be seen through a user's clothing and which do not resemble underwear; by relatively high levels of noise made from such products during use, such noise created from specific product construction materials; and by an overall "artificial" visual appearance of such products when viewed by the user and also by third parties. Such "artificial" look can result from the use of plastic, nonwoven material sheets, and sheet bonding arrangements common to such products, but which are necessary for cost-effective, nonwoven material sheet construction.

In their simplest forms, such garment-like articles frequently include at least a liquid permeable topsheet layer for placement directly next to the user's skin, at least one absorbent core layer subjacent the topsheet layer, and a liquid impermeable backsheet layer subjacent the absorbent core layer. The topsheet layer allows for body exudates to pass from the user into the one or more absorbent core layers of the absorbent article. The liquid impermeable backsheet layer prevents leakage of body exudates out of the absorbent core layer, once the liquid or fluid has been absorbed by the article. The absorbent core layer retains such liquids or fluids until article removal and disposal. Such absorbent articles may further include liquid transfer or other liquid distribution and control layers, which are typically placed between the liquid permeable topsheet layer and the absorbent core layer. Such garments may be sold in a sealed/permanently bonded, or prefastened format, or alternatively in an open refastenable format.

In use and when fastened, the absorbent articles include an interior user-facing surface which defines an interior space, and an exterior, garment-facing surface. The interior space is accessible from the exterior, through a waist opening and two leg openings. Construction seams are frequently placed in such products adjacent the opposing outermost waist edges for simplicity of manufacturing.

The topsheet layer may generally be of the same dimensions as the backsheet layer, or alternatively, shorter in some dimension, to allow the backsheet layer to be exposed to the user not only on the absorbent article exterior surface (if the product is of a simple design), but also along areas of the interior user-facing surface. Such backsheet layer may be stretchable or elastic to allow for a conformable fit of the absorbent article.

Further, while some garment-like article designs include only the simplified, three-layered chassis described above, or versions of such in which the absorbent core layer is sandwiched between the topsheet and backsheet layers with the backsheet layer extending into both waist regions, and far beyond the dimensions of the absorbent core layer, the three layers may also be present as part of an absorbent insert unit or absorbent "assembly", which itself is positioned between, or otherwise attached to at least one stretchable or elastic outer layer of the absorbent, garment-like article. The stretchable or elastic outer layer can extend laterally and longitudinally beyond the dimensional boundaries of the absorbent insert, such as into the waist region of the garment, or into areas that would contact a user's hips when the garment is worn. The stretchable or elastic outer layer may be in the form of a single panel that extends out beyond the absorbent insert in multiple directions, or alternatively, in the form of two or more separate panels, at least one for placement at the front waist region of the article, and at least one for placement at the back waist region (and hips) of the article, each adjacent opposing longitudinal end edges of the article absorbent insert. In such two panel designs, the front and back waist panels would be connected indirectly, via the absorbent insert itself, that forms the crotch region of the absorbent article. The absorbent insert essentially serves as a bridge in the crotch region, between the front and back waist regions/panels. Additional stretchable layers may be added to such a configuration, such as separate panels at the opposing hip regions, laterally alongside the waist panels.

These various garment-style absorbent article designs may be found for example in U.S. Pat. No. 4,205,679 to Repke et al., U.S. Pat. No. 4,701,171 to Boland et al., U.S. Pat. No. 4,906,243 to Dravland, U.S. Pat. No. 5,411,498 to Fahrenkrug et al., U.S. Pat. No. 5,643,396 to Rajala et al., U.S. Pat. No. 6,240,569 to Van Gompel et al., U.S. Pat. No. 7,011,653 to lmsangjan et al., U.S. Pat. No. 7,066,921 to Schmoker et al., U.S. Pat. No. 7,344,524 to Cazzato et al., U.S. Pat. No. 7,419,562 to Van Gompel et al., U.S. Pat. No. 7,604,624 to Veith et al., U.S. Pat. No. 8,043,274 to Mlinar et al., U.S. Pat. No. 8,147,476 to Veith et al., U.S. Pat. No. 8,246,598 to Vogt et al., United States Pat. Publications US20070208317 to Krautkramer et al., US20080134487 to Hartono, US 20100168705 to Stabelfeldt et al., US20110098668 to Thorson et al., US20110125122 to Thorson et al., US20120253310 to Hahn et al., Great Britain Pat. App. No. GB2165457 to McGhee, and European Pat. App. No. EP0878180 to Saito et al. each of which are incorporated by reference herein for purposes not inconsistent with this disclosure. As can be seen from the above references, it is known from the art to also utilize asymmetrical chassis designs for absorbent garments, in that the front and back waist regions or panels connected to an absorbent insert at the crotch, are of asymmetrical shapes. Such asymmetry has been associated with a more underwear-like appearance and sometimes, fit. The asymmetry may be created by similarly shaped panels having different length and/or width dimensions, or by truly dissimilar front and back panel shapes, that are bonded together at their lateral-most side edges. While such asymmetrically-shaped panels are desirable, they have sometimes been difficult to manufacture on a mass production line, depending on manufacturing method. Further, if such asymmetrically shaped panels are used, such configuration has been challenging for designs with elastic materials. There is therefore a need for absorbent articles and production methods which provide for use of asymmetrical panels made from body conformable elastic materials. There is a further need for such absorbent articles and methods of manufacture, which allow for different levels of elastic performance along laterally positioned panels.

It is also known to utilize elastic front panels with different lateral width dimensions than back panels, such that the formed bond seam between the two panels is situated off of the article sides or outermost, waist regions of the article, and forward on the article. For example, it is known to form seams of the article that are positioned towards a user's front crotch region (adjacent the commonly known "V"-region of a human body (between the users abdominal and pubic regions)). However, it has been difficult to produce such articles in an efficient and cost-effective way, without having to either utilize traditional and inefficient cut and placement techniques or nonconformable back panel materials. Such latter construction has sacrificed overall product fit, and has focused instead on reduction of front panel sagging during article use. For example, two different front and back panels demonstrate front panel elasticity and back panel non-stretchability respectively, as described in U.S. Pat. No. 5,440,764 to Matsushita. Further, individual cut and placement techniques of panels often demand machine-direction article production methods. In such forward-directed seam configurations, especially in refastenable products, there is therefore a need for article designs and production methods that can produce such articles efficiently. There is a further need to produce such asymmetrical articles with different levels of elastic performance between each of the front and back panels, and also with more comfortable leg opening features. While frontally positioned seams may also be found in refastenable articles in which a front seam is the result of an overlapping fastening component that is positioned in a closed position towards the front surface of the article, in such articles however, the elastic regions about the lateral sides of the fastening component demonstrate non-differentiated elastic functionality (that is the same level of elastic performance). There is a need therefore for refastenable articles with differentiated elastic functionality (that is elastic functionality which differs in laterally adjacent portions of the product).

Elastic material performance, as associated with a material's elastic "modulus", can vary as a result of different tensions applied to starting materials (and starting material relaxed lengths), starting material properties, and combinations thereof. There is a need for a method of production of elastic absorbent articles which takes advantage of attributes of elastic materials in order to locate features within such articles.

Use of various stretchable materials in absorbent articles is generally known. Stretchable materials have been used to create a close-to-body or conformable fit. Historically, such stretchable or elastic absorbent garments have relied on strand or film-based nonwoven laminate materials to provide the stretch attributes to targeted regions of such a garment. For example, such elastic materials have been described in some patent references for use only at the two hip regions of a garment, or alternatively, across the full length/width of the front and back waist panels. Such stretchable or elastic materials are typically symmetrical in their placement in a garment, such as at both hip regions, at both waist regions, or alternatively, completely surrounding the front and back waist or lower abdominal region (i.e. uninterrupted around the article, such that they circumscribe the article). References have also described differentiated elastic materials along an article longitudinal direction, such as different types or numbers of elastic materials along an article longitudinal direction. Occasionally, prior art references also describe the targeted deadening of stretchable or elastic materials placed over absorbent core layer assemblies, for a variety of product benefits. However, the remaining elastic regions laterally adjacent such absorbent core layers, and in directly-connected panels, often include similarly performing elastic components. There is therefore a need for asymmetrical absorbent articles which provide targeted placement of elastic components having different elastic functionality, adjacent one another. Such is desirable so as to provide a more conformable fit across different areas of a user's anatomy.

While such strand or film-based materials have provided needed stretch and subsequent conformance of a garment to a user's body, such garments have still frequently resembled baby or child care-related diapers in their appearance, even for adult-care focused products. This is often the result of the use of lateral-most side edge bond seams. That is, the front surface of the article is constructed of one front panel (excluding the crotch) and the back surface of the article is constructed of a separate singular panel (excluding the crotch). When such a fully elastic product is laid out in a fastened, but relaxed and flattened state, only one of such panels can be seen when the article is placed on a flat viewing surface. This attribute may not always be favored by the adult consumers. In traditional woven, male brief-style underwear, the visual emphasis of such garments is forward facing, and includes distinctively different front and back side details, rather than having a garment with "visually" symmetrical panels on both the front and back sides. As noted, such asymmetrical visual appearance poses manufacturing challenges, as asymmetrical elastic products (with different material properties between panels) are difficult to produce on machines at high speeds. There is therefore a need to develop absorbent garment-like articles and garment-like article production methods which allow for the production of absorbent garment-like articles having sufficient absorbent capacity and close-to-body fit, as well as which resemble traditional panty or brief-style underwear with asymmetrical front and back panels for adult consumers, without lateral-most, side edge bond seams.

The use of differently tensioned or basis weight elastic strands along an article longitudinal direction, and surrounding an article along a garment waist region, is also known. Such tensioned elastic strands circumscribe the waist region of the garment, with higher tensioned or basis weight elastic strands being positioned in areas where a closer body fit is desired along the article longitudinal direction. This is often accomplished by the use of different numbers of grouped elastic strands to circumscribe different regions of a waist region or different basis weight or tensioned elastic strands along the article longitudinal direction. However, such strands typically are described as being of the same number or functionality on both the front and back panel adjacent regions. Further, such elastic materials may create an awkward buckled visual appearance in an article that can be seen through a user's clothing. Such awkward buckled appearance hinders the ability of such articles to resemble traditional woven underwear. There is therefore a need for an adult care absorbent article design with different stretchable material across laterally adjacent areas of the front and back panels, that also reduces the opportunity for unsightly gathers to be seen through a user's clothing. There is still a further need for extensible or elastic absorbent articles, which during manufacture, utilize extensible or elastic panels of initially the same lateral dimensions for ease of article manufacture on a machine, but which as a result of manufacturing steps, results in a finished product that includes extensible or elastic panels of different lateral dimensions, and demonstrating either the same or different extensibility or elastic performance between the two laterally adjacent front and back panel areas.

Many of the designs of absorbent, garment-like articles previously described, have included elevated, or otherwise obvious bond seams at their lateral-most edges (when viewed from the front surface of the garment) in order to fasten two or multiple inelastic or elastic nonwoven panels to one another (such as the front and back panels). The bond seams (or "side seams" as they are often referred if at the lateral-most side edge) are frequently elevated, or extend from the surface of the garment at the outermost lateral side edges of the article (when the article is either viewed from the front surface in a relaxed, flattened state or viewed on a user's body). The bond seams frequently include alternating, patterned thermal or ultrasonic bond points, which accentuate the bond seams' presence. The bond seams may also include hardened regions as a result of the bonding techniques employed, which hardened regions may be felt by users as they are contacting the outermost, lateral side edges of the garments upon donning. Such pronounced bond seams are not typically present in traditional woven, cotton female panties or male, brief-style woven underwear, and therefore have also challenged manufacturers' ability to create underwear-like absorbent products. There is therefore a need to provide extensible or elastic, absorbent garment-like articles, which have reduced visual and tactile emphasis on manufacturing/bond seams, but which still provide desirable stretch characteristics of nonwoven materials in targeted regions.

In a further effort to create absorbent garment-like articles which demonstrate improved comfort, and which more closely resemble traditional adult underwear, manufacturers have altered the leg cut shapes of such articles so that the resulting leg openings rise higher on a finished/fastened garment than those of traditional child-care related, diapers with circular leg cuts/openings. While articles having such higher leg cuts have led to more comfortable garments, allowing for more flexibility in upper thigh movement without rubbing, such as can be seen in U.S. Pat. No. 7,011,653 to lmsangjan et al., there is still a need to include tailored conformability to such products, such as to provide targeted elastic functionality in specific laterally adjacent regions. There is also a need to enhance the visual association of such articles with that of traditional woven underwear. Such ergonomically designed, higher rise leg cuts may produce vertex-like structures along the leg opening peripheral edges. However, the bond seams in such articles are not aligned with the vertices or the apexes of such vertices of such leg openings. This non-alignment may lead to flaps of excess panel material extending from the lateral-most side edges or at the bond seams. There is therefore a need for absorbent article designs which provide for ergonomically shaped leg openings, comfortable and aesthetically-pleasing seam placement, and also for targeted elastic performance.

There have been at least two distinct, large-volume manufacturing methods commonly described in the patent literature to produce such garment-like absorbent articles, each having their respective advantages and disadvantages. In the first method, which can be described as a machine-direction process (or MD process), each article (and layers making it up) is moved along its main longitudinal axis or longitudinal direction, throughout the manufacturing process. Such a process has enabled with relative ease, the production of articles with high rise leg cuts as described. The second, cross-machine direction process (or CD process) has often enabled the ease of production of elastic articles with desired fit attributes. In such a CD process, each absorbent article is moved throughout the process along the article transverse direction (transverse axis). As a result, similarly performing elastic sheet materials may be employed for the front and back panels along the transverse direction, allowing for ease of large volume production of finished articles with front and back panels having the same lateral width dimensions. Such a process however, has posed challenges for the production of high rise and off-center ergonomic leg openings, in combination with targeted elastic regions (differentiated by region) based on similar layer starting dimensions. Therefore, there is a need for CD manufacturing processes that allow for the manufacture of articles having both targeted elastic performance (differentiated by article region) at laterally adjacent regions of an article, and also high rise leg cut openings, but which method allows for similar starting dimensions (transverse direction width) of front and back panels in a manufacturing process. There is a further need for a CD-produced fully elastic garment with seams that are positioned on an article front surface, rather than at an article's lateral-most side edge, so as to be more visually similar to traditional underwear.

A general example of a prior art, disposable elastic and absorbent article that is produced in a CD process is illustrated in FIGS. 1A-1D. In particular, FIGS. 1A, 1B, 1C, and 1D show respectively a front surface perspective view and lateral side perspective view, a top planar (unfastened) view, and a cross-sectional view of such prior art absorbent undergarment 10. Such undergarment 10 would typically be used to address issues of incontinence, but may also be used for baby and child care product applications.

The absorbent undergarment 10 in FIGS. 1A-1D has a longitudinal direction L, a transverse direction T ending in lateral-most side edges 24, and a depth direction Z. In the illustrated embodiment, the undergarment has relatively symmetrical back and front side panels 12, 14 although such may not always be the case as previously described. For example, the shape of the front and back side panels may not be the same, as the back panel 12 may have an overall larger surface area than the front to cover hip areas when in a fastened state. However, the transverse direction width of the two panels, at least starting out, is the same. With limited exceptions as have previously been noted with respect to U.S. Pat. No. 5,340,424 which describes a nonstretchable back panel, the final transverse width dimensions of the front and back panels have been the same for articles produced using a CD-type process.

The back and front panels are connected indirectly via a crotch region 20 and directly along the bonded lateral-most side edges 24. In the illustrated embodiment, the front and back panels include various groupings of elastic strand features 42, 44 shown in phantom lines (and the same elastic functionality in adjacent lateral zones, but varying along their panel heights or longitudinal direction L). That is, the articles have differentiated elastic performance in zones along their lengths based on either the different strand grouping number, spacing, basis weights or other attributes of strands along the article longitudinal direction, but demonstrate the same elastic performance at the same height level of each laterally adjacent panel. The elastic front and back panels in the figures are constructed from laminates of elastic stranded materials that have been bonded in their stretched state to nonwoven sheets on each side of the strands. They also include the same lateral width dimensions both during and following article 10 manufacture (as seen specifically in FIG. 2). That is, the lateral widths of the front and back panels before production are the same. The lateral widths of the front and back panels after production are also the same, although the before and after lateral widths may differ.

The front and back panels can actually be made of a unitary laminate sheet construction (as shown) on which an absorbent insert 16 is placed, or of separate front and back panel sheets that are both connected to opposing longitudinal ends of the absorbent core insert 16. Either way, the front and back panels are cut for leg openings and bonded together during manufacture, at their lateral-most side edges 24 by outwardly extending or elevated side bond seams 25, thereby forming the waist region 18, the two leg openings 26 often formed with ruffled edges, and a waist opening 28. The waist opening 28 is circumscribed by a waist edge 22 (which may include an integral or separate waist band). In use, the waist region 18 circumscribes a user's lower abdominal region and may, depending on design, pass over or about a user's hips. Alternatively, while not shown in this figure, but which is seen in the reference U.S. Pat. No. 5,411,498 to Fahrenkrug et al., elastic panels may be positioned instead over a user's hips and not the majority of the waist region.

The side bond seams 25 are typically created by thermal, pressure, or ultrasonic bonding techniques as are known in the art, but may also be created by adhesive or alternative bonding methods. The CD produced prior art undergarment 10 is folded during article formation prior to side seam bonding, about fold line 40 (seen in FIG. 2) with one panel brought over the other. While not illustrated, the prior art undergarment 10, may include refastenable features rather than the semi-permanent, elevated side bond seams 25 which semi-permanent side bond seams are not designed to be opened and closed repeatedly. The leg openings may further include around their peripheral edges, elastic components 38 for closer fit around a user's upper thighs. Following bonding at side seams, the individual articles are cut from the moving sheets, and are then free to be folded and packaged as desired.

The illustrated prior art undergarment 10 includes an absorbent core insert unit/assembly 16 (as seen in FIG. 1D), which itself includes a combination of a user-facing liquid permeable topsheet layer 30, one or more absorbent core layers 32 and a liquid impermeable, garment-facing backsheet layer 34. As previously described, one or more stretchable or elastic outer layers 36 (such as the front and back panels), can be placed immediately adjacent the liquid impermeable backsheet layer 34 (in the undergarment Z direction) which provides extensibility attributes at least in areas of the undergarment 10 beyond the lateral and longitudinal dimensions of the absorbent insert unit 16, and makes up the front and back panels 12, 14. The elastic outer layer may be made for example, of an elastic film or film laminate material or a differentiated elastic stranded laminate portions 42, 44 as shown. As used herein, the term "differentiated" shall refer to either an elastic laminate in which different regions or zones of the same laminate include materials having different elastic functionality, or alternatively two different elastic materials within the same article. For example, an elastic strand laminate may include different types, numbers, or groupings of elastic strands along a laminate longitudinal direction, elastic strands having different tensions along the laminate longitudinal direction, or elastic strands of different decitex along the laminate longitudinal direction.

As also seen in FIGS. 1A-1B, the front and back panels 12, 14 of the prior art CD produced undergarment 10 (which form the leg openings 26), intersect at an upper portion of the leg openings 33, located at each lateral-most side edges 24 of the undergarment 10, once the undergarment has been bonded together by side bond seams 25. These upper leg circular opening portions 33 may be aligned with the side seam bonds 25, which are both positioned at the lateral-most side edges 24 of the undergarment, when viewed from the front surface of the article. In this fashion, the visual prominence of the side bond seams 25 is accentuated, as the bond seams protrude outwardly at the lateral-most side edges 24. This protrusion can lead to friction upon contact, along the lateral-most side edges of the absorbent article. Further, this bond seam 25 placement requires contact of the opposing interior surface seam line (on the fastened article, interior surface) with a user's outer waist regions during article donning and normal use. Since this interiorly-situated seam line is in a region of the absorbent article that may experience the largest extension and possible friction or rubbing during use, it is likely that such contact may be sensed by a user and may lead to discomfort. Further, such leg opening positions restrict upper thigh movement causing frictional contact with the leg opening side edges.

A stylized view of prior art CD manufacturing method steps for producing the prior art elastic and absorbent garment 10 is illustrated in FIG. 2. As can be seen in the Figure, the panty or brief style absorbent garment is formed from a chassis including stretchable material 36 along an assembly line 50. The sheets that will eventually become absorbent articles 10 are aligned along their transverse directions as they move along the assembly line 50 in the machine. The absorbent article longitudinal directions are perpendicular to the direction of article travel through the process. As indicated by the arrows 46, 47 being of the same length dimensions at each opposing waist portions (front and back panels 12, 14) of the garments in the process, approximately the same degree of tension (or machine draw) t1, t2 is either present or applied to the front and back side panel materials during production, in order to stretch the chassis material to the same extent at each opposing side during the process. The starting lateral width dimensions W1, W2 of the two panels in the article transverse direction T, are shown as being the same during production, (although as previously stated, the overall surface area dimensions of each panel need not be the same starting out). In the illustrated article, following production, the respective lateral width dimensions of the two panels are generally the same (except as previously noted), although the widths may be different between the starting and final product forms. That is, W1 is the same as W2, and W1' is the same as W2'. The articles are formed with the absorbent core insert 16 on the one or two stretchable panels, the articles being stretched as desired uniformly along the front and back panels, folded, bonded and then cut into individual products, which appear as the final article 54. The individual articles 54 are allowed to relax, resulting in front and back elastic panels having equal overall lateral dimension and aligned widths that are connected at side bond seams 25. The illustrated open article 52, while not actually appearing as a separated individual open article during the process, is provided for ease of reference in order to understand lateral width dimensions throughout the process. The finished articles demonstrate the same transverse direction T, elastic functionality on both the front and back panels 12, 14, as a result of the same elastic stranded laminate portions 42, 44 in each panel. The leg openings in the prior art production methods are created by die cutting either a circular-like shape or an ergonomic shape as previously described, from each panel of the article and appear at the lateral-most side edge 24. There is therefore a need for CD-article production methods and CD-produced absorbent articles which provide the desired panel dimension and elasticity differentiation between adjacent lateral article regions, so as to enhance user comfort.

SUMMARY OF THE INVENTION

In one embodiment of the invention an absorbent article for encircling a user's lower abdominal region, has a longitudinal direction, a central longitudinal direction, a transverse direction ending in opposing lateral-most side edges, and a depth direction. The absorbent article includes an absorbent article front surface and an absorbent article back surface, two leg openings having opening edges, and a waist opening defined by a waist edge, with a minimum transverse direction width when the absorbent article is in a relaxed and flattened state. The absorbent article includes an absorbent core insert having a liquid permeable topsheet layer, a liquid impermeable backsheet layer, and at least one absorbent core layer sandwiched between the liquid permeable topsheet layer and the liquid impermeable backsheet layer. The absorbent core insert also has two opposing longitudinal direction ends and opposing lateral direction side edges extending between the opposing longitudinal direction ends. The absorbent core insert forms the crotch portion of the absorbent article. The absorbent article further includes asymmetrically shaped front and back panels which together form the waist edge of the absorbent article waist opening. The front panel is elastic along the absorbent article transverse direction. The back panel is at least extensible along the absorbent article transverse direction, it being understood that the back panel may be either extensible or elastic. The front and back panels are bonded to opposing longitudinal direction ends of the absorbent core insert, and further bonded to each other along bond seams situated inwardly from the absorbent article opposing lateral-most side edges and along the absorbent article front surface. A distance between each bond seam and the closest lateral-most side edge of the absorbent article is between about 2.5% and 25% of the minimum transverse direction width of the waist edge of the absorbent article. Alternatively, the distance can be between about 5% and 22.5% of the minimum transverse direction width of the waist edge of the absorbent article. The minimum transverse direction width is measured at the narrowest point between the opposing lateral-most side edges of the absorbent article when in a relaxed and flattened state.

In an alternative embodiment, the front and back panels are both fashioned from elastic materials that are elastic in the article transverse direction. In a further alternative embodiment, the front and back panels are of different elastic materials that are elastic in the article transverse direction, such differences based on either different levels of elasticity (elongation and/or retraction power/retractive force), different polymers, or different material structures. In a further alternative embodiment, the front panel demonstrates higher levels of elasticity (retractive force) than the back panel. In a further alternative embodiment, the front panel demonstrates the ability to retract to a narrower transverse direction width than the back panel.

In yet a further alternative embodiment, the absorbent article has leg openings, with each leg opening including a vertex portion along the leg opening edge, which vertex is visible along the absorbent article front surface. Each vertex portion has an apex along the absorbent article front surface. The bond seams extend from the apex of the vertices to a point on the waist edge also located along the absorbent article front surface, such that the distance between a bond seam and the closest lateral-most side edge is between about 2.5% and 25% of the minimum transverse direction width of the waist edge of the absorbent article. In an alternative embodiment, the front and back panels of such an article with high rise leg openings, are both elastic along the absorbent article transverse direction. In a further alternative embodiment, the front and back panels of such an article with high rise leg openings are formed of different elastic materials. In still a further alternative embodiment, the front and back panels of such an article with high rise leg openings, are of different elastic materials having different levels of elasticity (retraction), with said front panel demonstrating higher levels of elasticity (retraction) than said back panel under similar conditions.

In a further alternative embodiment, the front and back elastic panels are selected from the group consisting of elastic film and nonwoven laminates, elastic strand and nonwoven laminates, pre-formed elastic fibers and nonwoven laminates, elastic films, elastic nonwoven sheets, laminates of the foregoing materials and combinations of the foregoing materials. In yet a further alternative embodiment, the front and back elastic panels are selected from the group consisting of film and nonwoven laminates, extruded strand and nonwoven laminates, and pre-formed elastic fibers and nonwoven laminates.

In another alternative embodiment, the absorbent article leg openings are elongated along the absorbent article longitudinal direction. In still a further alternative embodiment, the vertices of high rise leg openings in the absorbent article, are in the shape selected from the group consisting of inverted V-shaped and inverted U-shaped configurations.

In still another alternative embodiment of the absorbent article with high rise leg openings, the distance between a bond seam and the closest lateral-most side edge is between about 5% and 22.5% of the minimum transverse direction width of the waist edge of the absorbent article.

In yet a further alternative embodiment of the absorbent article of the invention, the front and back panels demonstrate different elastic functionality as a result of being the same material, bonded at said bond seams under different levels of tension, with said front panel bonded at higher levels of tension than said back panel. In still a further alternative embodiment of the invention, the front and back panels on the absorbent article demonstrate different retractive power/force.

In a further alternative embodiment, the bond seams are constructed with temporarily bonded sheet materials. In still a further alternative embodiment, such bond seams are temporary bond seams and/or include frangible bonds. In yet another alternative embodiment, fastening components for refastening the absorbent article, are attached to the front and back panels. In still another alternative embodiment, fastening components for refastening the absorbent article, are attached to the front and back panels at a location at or adjacent to the bond seams. In yet a further alternative embodiment, tearable seams or lines of weakness are included on the absorbent article. In another alternative embodiment, such tearable seams or lines of weakness are separate from, and adjacent to the bond seams.

In an alternative embodiment of the invention, a method of making an absorbent article includes the steps of a) producing a first sheet of an elastic material having a longitudinal and transverse direction, with the first sheet being elastic in at least the transverse direction, b) producing a second sheet of at least an extensible material (alternatively elastic) having a longitudinal and transverse direction, with the second sheet being at least extensible in at least the transverse direction; and placing the first and second sheets in parallel along their transverse directions on an absorbent article production line; c) producing an absorbent core insert having opposing longitudinal direction ends for attachment to the sheets of elastic and at least extensible materials, and opposing lateral side edges extending between the opposing longitudinal direction ends, and bonding the opposing longitudinal direction ends of the absorbent core insert to the sheets of elastic and at least extensible material in a configuration that is perpendicular to the first and second sheet transverse directions while such first and second sheets are under desired levels of tension; d) moving the bonded sheets and absorbent core insert through a manufacturing process on the absorbent article production line, along the sheet transverse directions such that differential tensions are applied along the transverse direction to the first sheet of elastic material compared with the at least extensible material, the tension applied to the elastic material being larger than that applied to the at least extensible material; e) at some point, cutting elongated leg opening shapes along the sheets' longitudinal direction and adjacent the opposing lateral side edges of the absorbent core insert so that the highest point of the cuts will align with side bond seams; f) bringing the elastic material sheet and the at least extensible material sheet together to form an absorbent article blank having elongated leg openings with distinct vertex configurations, and subsequently bonding the material sheets to one another along side bond seams that are generally aligned with the sheets' longitudinal direction and aligned with the vertex configurations in order to form an absorbent article with the elastic sheet and the at least extensible sheet having the same transverse direction width, while maintaining the sheets under their respective tensions; g) cutting the absorbent article from the absorbent article blank and removing such tension such that the elastic sheet transverse direction width narrows with respect to the at least extensible sheet transverse direction width as a result of differential levels of retraction of said sheets, whereby the bond seams rotate from a lateral-most side location to a forwardly positioned location off of the absorbent article lateral-most side edge.

In an alternative embodiment of the method, the first and second sheets of material are both elastic. In another embodiment of the method, the first and second sheets of material are formed of different elastic materials, such as for example, elastic materials that have different retractive power or different levels of retraction, different elongations, different chemical compositions, different basis weights, or different layered structures.

In a further alternative embodiment, the bond seams are constructed with temporarily bonded sheet materials. In still a further alternative embodiment, such bond seams are temporary bond seams and/or include frangible bonds. In yet another alternative embodiment, fastening components for refastening the absorbent article, are attached to the front and back panels. In still another alternative embodiment, fastening components for refastening the absorbent article, are attached to the front and back panels at a location at or adjacent to the bond seams. In yet a further alternative embodiment, tearable seams or lines of weakness are included on the absorbent article. In another alternative embodiment, such tearable seams or lines of weakness are separated from, and adjacent to the bond seams.

In a further embodiment, a refastenable absorbent article for encircling a user's lower abdominal region includes a longitudinal direction, a central longitudinal direction, a transverse direction ending in opposing lateral-most side edges, and a depth direction. The absorbent article includes an absorbent article front surface and an absorbent article back surface, two leg openings, and a waist opening defined by a waist edge with a minimum transverse direction width when the absorbent article is in a relaxed and flattened state. The absorbent article further includes an absorbent core insert including a liquid permeable topsheet layer, a liquid impermeable backsheet layer, and at least one absorbent core layer sandwiched between the liquid permeable topsheet layer and the liquid impermeable backsheet layer. The absorbent core insert includes two opposing longitudinal direction ends and opposing lateral direction side edges extending between the opposing longitudinal direction ends, the absorbent core insert forming the crotch portion of the refastenable absorbent article. The refastenable absorbent article also includes asymmetrically shaped front and back panels which together form the waist edge of the absorbent article waist opening. The front panel is elastic along the absorbent article transverse direction, and the back panel is at least extensible along the absorbent article transverse direction (alternatively elastic). The front and back panels are respectively bonded to opposing longitudinal direction ends of the absorbent core insert, and further attached to each other along at least temporary bond seams situated inwardly from the absorbent article opposing lateral-most side edges and along the absorbent article front surface.

The refastenable absorbent article further includes leg openings, each having a vertex portion along the opening edge, each vertex portion having a distinct apex along the absorbent article front surface. The at least temporary bond seams extend from the apex of the vertices to a point on the waist edge located along the refastenable absorbent article front surface, such that the distance between the at least temporary seam and the closest lateral-most side edge being between about 2.5% and 25% of the minimum transverse direction width of the waist edge of the refastenable absorbent article. The refastenable absorbent article further includes fastening components attached to the front and back panels, positioned either on or adjacent to the at least temporary bond seams. In an alternative embodiment, such temporary bond seams are formed using perforations and/or lines of weakness based on ultrasonic or adhesive bonding methods.

In yet another alternative embodiment, the refastenable absorbent article front and back panels include lateral-most side edges and the absorbent article includes the fastening components for fastening and unfastening the absorbent article on or adjacent the front and back lateral-most edges, the fastening components selected from the group consisting of mated adhesive fastening components and mated hook-and-loop fastening components.

In still another alternative method of manufacture, a method of making an absorbent article includes the steps of a) producing a first sheet of an elastic material having a longitudinal and transverse direction, with the first sheet being elastic in at least the transverse direction, b) producing a second sheet of at least an extensible material (alternatively elastic) having a longitudinal and transverse direction, with the second sheet being at least extensible in at least the transverse direction; and placing the first and second sheets in parallel along their transverse directions on an absorbent article production line; c) moving the first and second sheets through the manufacturing process on the absorbent article production line, along the sheet transverse directions such that differential tensions are applied along the transverse direction to the first sheet compared with the second sheet, the tension applied to the first sheet being larger than that applied to the second sheet; d) producing an absorbent core insert having opposing longitudinal direction ends for attachment to the first sheet and second sheet, and opposing lateral side edges extending between the opposing longitudinal direction ends, and bonding the opposing longitudinal direction ends of the absorbent core insert to the first sheet and the second sheet in a configuration that is perpendicular to the first sheet and second sheet transverse directions while such first and second sheets are under desired levels of tension; e) cutting elongated leg opening shapes along the sheets' longitudinal direction so that the highest point of the cuts will align with bond seams; f) bringing the first sheet and second sheet together to form an absorbent article blank, and subsequently bonding the material sheets to one another along bond seams that are generally aligned with the sheets' longitudinal direction in order to form an absorbent article with the first sheet and the second sheet having the same transverse direction width, while maintaining the sheets under their respective tensions; g) cutting the absorbent article from the absorbent article blank and removing such tension such that the first sheet transverse direction width narrows with respect to the second sheet transverse direction width as a result of differential levels of retraction in or on the sheets, whereby the bond seams rotate from a lateral-most side location to a position location inward of the lateral-most side edge.

BRIEF DESCRIPTION OF THE DRAWINGS

A full and enabling disclosure of the present invention is set forth more particularly in the remainder of the specification, including reference to the accompanying figures, in which:

FIG. 4 (including FIGS. 4A-4F) is a stylized, sequential view of various CD manufacturing steps for producing the absorbent article of FIG. 3A in accordance with the invention.

DEFINITIONS

Figure 1A:
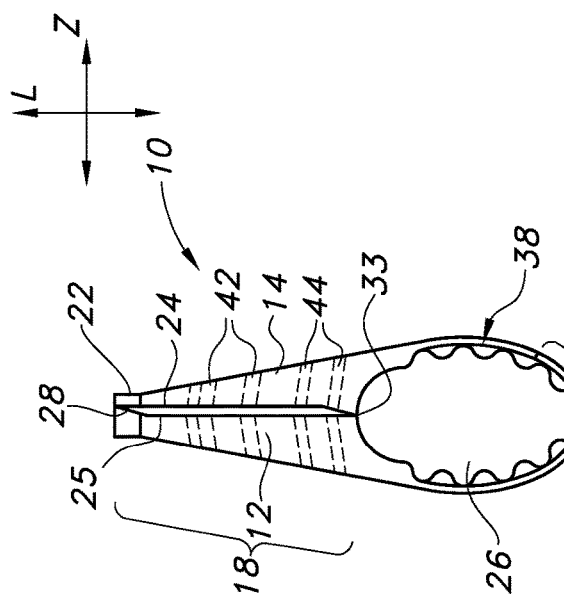
FIG. 1A illustrates a front surface, perspective view of a prior art absorbent, garment-like article, in the form of an incontinence pant.
Figure 1B:
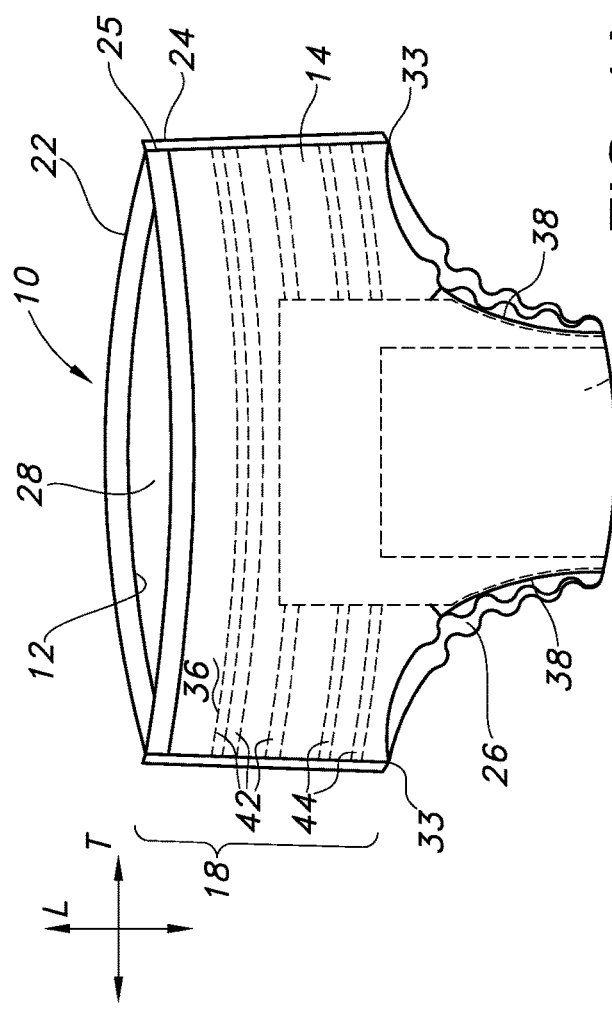
FIG. 1B illustrates a side perspective view of the prior art incontinence pant of FIG. 1A.
Figure 1D:
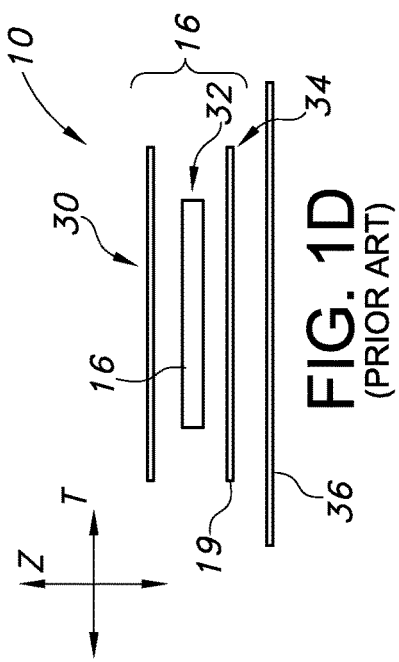
FIG. 1D illustrates an exploded cross-sectional view of a portion of the prior art incontinence pant of FIG. 1A taken along line 1D-1D.
Figure 1C:
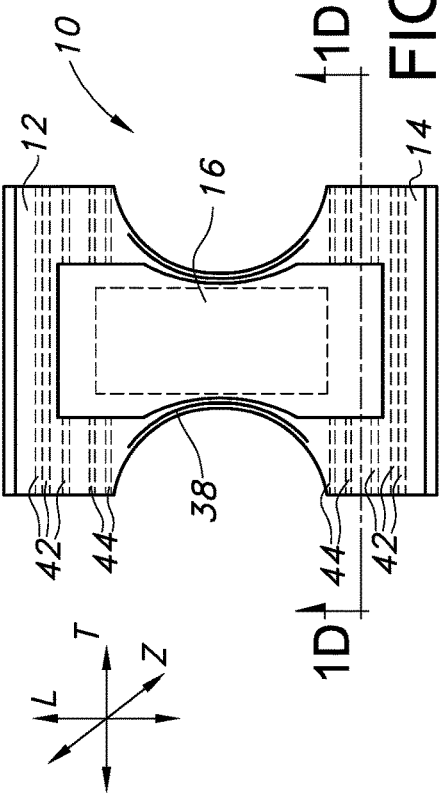
FIG. 1C illustrates an unfastened (unbonded), top plan view of the prior art incontinence pant of FIG. 1A in an opened configuration.
Figure 2:
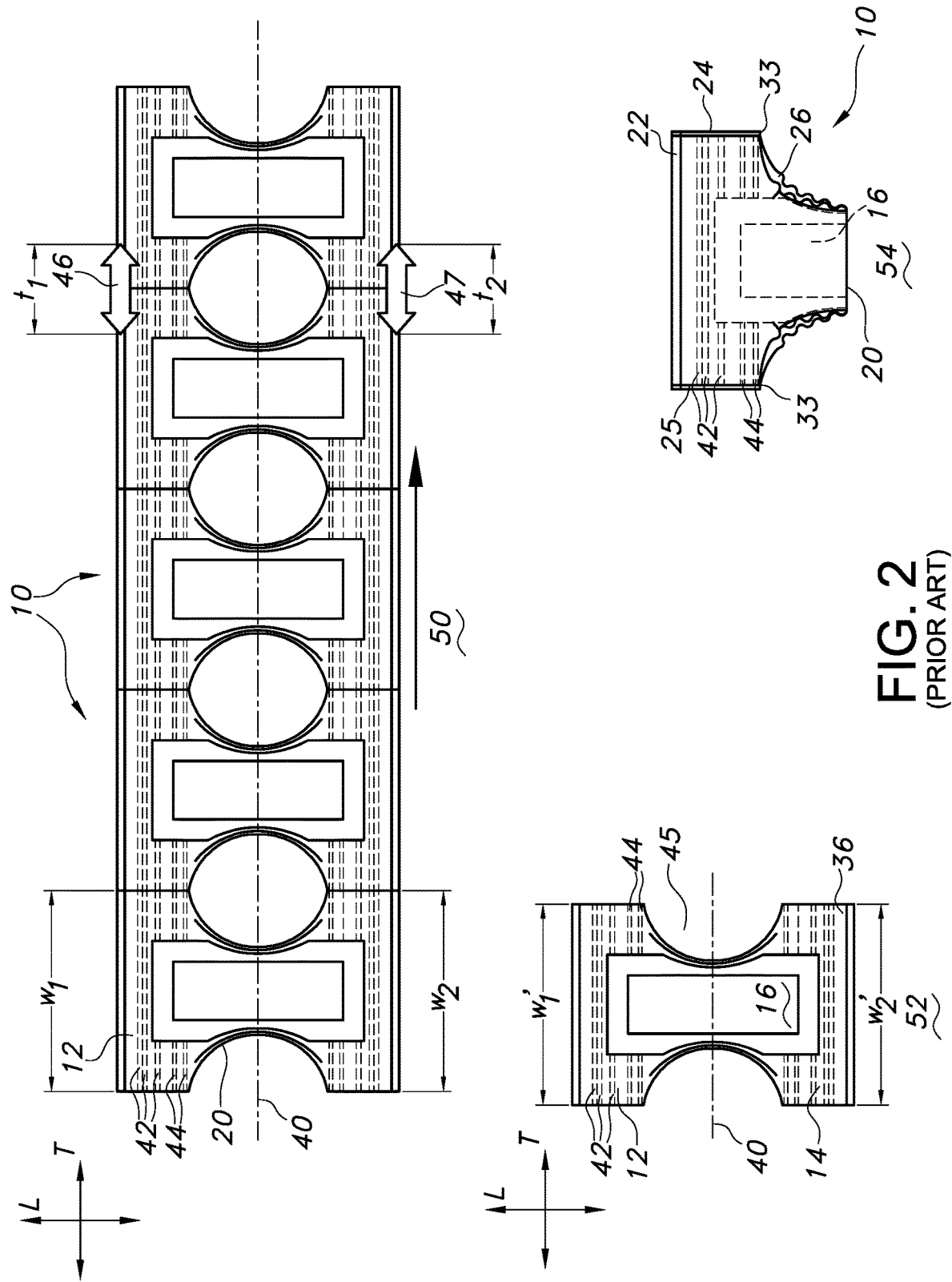
FIG. 2 illustrates a stylized, sequential step view of prior art CD manufacturing steps for producing the prior art incontinence pant of FIG. 1A.

As used herein the term "nonwoven fabric or web" refers to a web having a structure of individual fibers or threads which are interlaid, but not in an identifiable manner as in a knitted fabric. Nonwoven fabrics or webs have been formed from many processes such as for example, meltblowing processes, spunbonding processes, coform processes, hydroentangling, and bonded carded web processes (such as through-air bonded carded webs or TABCW).

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed fibers. Such a process is disclosed, for example, in U.S. Pat. No. 3,849,241 to Butin, et al., which is incorporated herein in its entirety by reference thereto. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki. et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and 5,382,400 to Pike, et al., which are each incorporated herein in their entirety by reference thereto. Spunbond fibers are generally not tacky when they are deposited onto a collecting surface. Spunbond fibers may sometimes have diameters less than about 40 microns, such as between about 5 to about 20 microns.

As used herein, the term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 5,284,703 to Everhart, et al., and U.S. Pat. No. 5,350,624 to Georger, et al., each of which are incorporated herein in their entirety by reference thereto.

As used herein, the term "extensible" shall be used interchangeably to mean "stretchable", and generally refers to a material or article that stretches or extends in the direction of an applied force (e.g., transverse or longitudinal direction by about 25% or more, alternatively, 50% or more, in some embodiments about 100% or more, and in some embodiments, about 200% or more of its relaxed length or width).

As used herein, the term "elastic" generally refers to an extensible material or article that, upon application of a stretching force, is stretchable in at least one direction (e.g., transverse or longitudinal direction), and which upon release of the stretching force, contracts/returns at least a portion of its stretched length, desirably to approximately its original dimension. For example, such a material or article may be elongated by at least 25% of its relaxed length and will recover, upon release of the applied force, at least 10% of its elongation (its elasticity level). In another example, the stretched material or article may contract or recover at least about 50%, and even more desirably, at least about 80% of its stretched length. Elastic materials or articles are by definition, extensible, but extensible materials are by definition, not necessarily elastic. An extensible material or article may be inelastic. A material or article that is described in this application as being "at least" extensible, implies that such material or article at least extends as defined, but may also retract as with elastic materials. An elastic material may include films, fiber-based materials, scrims, foams, woven materials, nonwoven materials and laminates of the foregoing. Various examples of extensible and elastic materials (and other garment layers) for use with the present disclosure may be found in U.S. Pat. No. 7,855,316 to Meyer et al., which is hereby incorporated by reference thereto in its entirety, for all purposes not inconsistent herewith.

Material may be tested for its elastic properties using a cyclical testing procedure. In particular, 2-cycle testing may be employed to 100% defined elongation. For this test, the sample size may be 3 inches (7.6 centimeters) in the cross-machine direction by 6 inches (15.2 centimeters) in the machine direction. The grip size may be 3 inches (7.6 centimeters) in width. The grip separation may be 4 inches (10.2 centimeters). The samples may be loaded so that the machine direction of the sample is in the vertical direction. A preload of approximately 20 to 30 grams may be employed. The test may pull the sample to 100% elongation at a speed of 20 inches (50.8 centimeters) per minute and then immediately (without pause) return the sample to 0% elongation at a speed of 20 inches (50.8 centimeters) per minute. The results of test data are desirably from the first and second cycles. The testing may be performed on a Sintech Corp. Constant rate of extension tester 2/S with a Renew MTS mongoose box (control) using TESTWORKS 4.07b software (Sintech Corp., of Cary, NC) and conducted under ambient conditions.

As used herein, the phrase "retractive force" shall refer to the retractive force exhibited by the elastic fabric area one minute after stretching to 90% of the elongation of the elastic fabric area, and is suitably determined as set forth below.

The retractive force of an elastic fabric area according to the present invention is determined on a test sample having a width of 1 inch and a length of 3 inches. A test apparatus having a fixed clamp and an adjustable clamp is provided. The adjustable clamp is equipped with a strain gauge commercially available from S.A. Mieier Co. under the trade designation Chatillon DFIS2 Digital force gauge. The test apparatus can elongate the test sample to a given length. One longitudinal end of the test sample is clamped in the fixed clamp of the test apparatus with the opposite longitudinal end being clamped in the adjustable clamp fitted with the strain gauge. The test sample is elongated to 90 percent of its elongation (as determined immediately below). The retractive force is read from the digital force gauge after 1 minute. At least three samples of the elasticized area (fabric) are tested in this manner with the results being averaged and reported as grams force per inch width. The elongation of an elastic fabric for use in the retractive force test above is suitably determined as follows. A 1 inch by 4 inch wide long elastic fabric is provided. The central 3 inch (7.62 cm) area of the sample is marked. The test sample is then stretched to its maximum length, and the distance between the marks is measured and recorded as the "stretched to stop length". The percent elongation is determined according to the following formula:

$$(\text{Stretched to stop length(in inches)} - 3)/3 \times 100.$$

If a 1 inch by 4 inch elastic fabric is not available, the largest sample possible (but less than 1 inch by 4 inch) is used for testing with the test method adjusted accordingly.

As used herein, the term "bonded" refers herein to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "absorbent article" refers herein to a garment-like article that can be worn so as to encircle about a user's lower abdominal area, and which can capture and retain liquid or fluid waste exuded from a user's body, such as menses, blood, feces, or urine. Such a garment-like article includes for example, a disposable absorbent diaper, pant, panty, or brief, and may encompass baby care, child care, feminine care and adult care incontinence product applications. Desirably in one embodiment, such an absorbent article encircles a user's waist and hips.

As used herein the term "lower abdominal" shall comprise the area of the human body encompassing a position from near a user's belly button to the crotch region between the user's legs. Such area shall encompass the genital and buttocks region of the human body, at least a portion of the waist region of the human body, and may further include the hip regions of the human body.

As used herein, the term "refastenable" shall encompass a garment-style, absorbent article that may be repeatedly fastened and unfastened during use by employing a fastening mechanism such as a tape, or hook-and-loop style mechanism. As used herein, the term "prefastened" shall encompass a garment-style, absorbent article that may be applied to a user without having to undo or connect a fastening mechanism (such as adhesive tapes or hook-and-loop-style mechanisms. Such a "prefastened" configuration may also include an easy tear feature such as a perforation or other feature which enables the article to be opened upon ripping along a pre-determined line of weakness. The term "open refastenable" shall refer to a garment-style, absorbent article which is in its unfastened condition.

As used herein, the term "relaxed" state or condition shall refer to an absorbent article in an untensioned state, such as for example when a finished bonded and/or fastened article is in a flattened, fully laid-out configuration on a level, planar surface without the article being folded over itself, or exposed to any external tension or compression applied thereto.

As used herein, the term "front surface" shall refer to that portion of an absorbent article which is normally placed over the user's front, lower abdominal region and which is visible in a relaxed state. As used herein, the term "back surface" shall refer to that portion of an absorbent article which is normally placed over the user's back, buttocks region and is visible in a relaxed state.

As used herein, the terms "comprise", "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "has" and/or "have", and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. For the purposes of this application, like features may be represented by like numbers between the figures. While not illustrated in most figures except where additional location emphasis is desired, it should be understood that traditional absorbent article construction adhesive (or other bonding technology) is to be used to join the various layers of the described articles together.

Generally speaking, the absorbent personal care articles of the present invention are ideally suitable for use as baby and child care diapers, feminine care panties, and adult incontinence, garment-like absorbent articles. Such are particularly suitable for older child care, feminine care and adult incontinence garment-style, absorbent articles, as the designs position body facing, potentially friction causing, interiorly situated seam lines away from a user's outer waist regions, and towards a user's "V"-line areas (or natural body crease areas, near the frontal crotch region and between the lower abdominal and pubic area), and creates a visual resemblance to traditional woven underwear. The bond seams of either two differentiated elastic front and back panels, or elastic front and extensible back panels, are moved from traditionally, lateral-most article side edge configurations, to locations closer to the center longitudinal direction of the article, whereby enlarged, elastic or extensible back panel surface coverage is provided. In one embodiment, such bond seams are moved forward along the front surface to a location closer to the center longitudinal direction of the article. In particular, by attaching two elastic panels to an absorbent insert, with each panel demonstrating either an initially different level of elasticity (or retractive power) and maintained under tensions (or different tensions) during article production; or having the same level of elasticity and having been subjected to different levels of tension (i.e. machine draw) during a manufacturing process and ultimately leading to different lateral (transverse) dimensions between front and back panels upon article manufacture, an article is created that includes differentiated elastic characteristics along the lateral directions (transverse direction width) and, with such panel attachment being maintained at a bond seam located desirably inwardly/forward of the lateral-most side edges of the prefastened absorbent article. In any event, in one embodiment, the front elastic panel material desirably demonstrates ultimately a larger elastic recovery (or retractive power) than the back panel, and is desirably maintained under greater tension/elongation during the manufacturing process. For example, in one embodiment, the front panel retracts at least 25% of its initial length, while the back panel retracts 10% of its initial length. In one embodiment, the front elastic panel has a shorter fully retracted width dimension, than the fully retracted width dimension of the back elastic or extensible panel. It should be understood that an extensible but inelastic material would not retract at all. A more underwear-like and comfortable absorbent article is therefore produced. Alternatively, such article may be created with one distinct back panel of extensible material, and another front panel of elastic material.

A method is also provided in which an absorbent article is created that utilizes two differentiated elastic panels that have been exposed to differential tension levels during manufacture. While the panels include the same lateral width dimensions during early stages of manufacture and upon side seam bonding, upon individual article separation (cutting from absorbent article blanks), the articles are allowed to relax, which subsequently allows the differentially tensioned panels to retract at different levels, with the front or otherwise selected panel retracting to a greater extent. This retraction causes the previously positioned side bond seams to rotate from the articles' lateral-most side edges to positions more toward an article's central longitudinal direction, and desirably forward on the article (and on the front surface) along with the leg openings. Such leg openings desirably in one embodiment, include vertices along their peripheral edges that are aligned with the bond seams. The lateral-most side edges are then, following this rotation, made up of only the back panel material, rather than both the front and back panels, as was the case during the early stages of the article manufacture (prior to cutting of individual articles and article separation). This relaxation/retraction results in the production of asymmetrical front and back panels, with the final (post formation) front panel desirably having a narrower transverse direction width than the final (post formation) back panel. It should be appreciated, that while the focus of this disclosure is to enable the movement of both a side bond seam and a leg opening having a distinct vertex, forwards to a front surface of an absorbent article, such methods may also be used to move such side seams and vertex-containing opening towards the back surface of an article if desired, producing an asymmetrical article with a larger transverse direction width front panel and a narrower transverse direction width back panel.

Such comfort and fit is enhanced by the inclusion of ergonomically designed leg openings (elongated openings including distinct vertex-like side edge portions) also visible along the front surface of the article, in which the inwardly or forwardly directed front surface facing seams between front and back side panels meet at the pointed vertex or uppermost, elongated curved feature, in the high rise, leg openings formed by the two panels. The seams extend from the apex of the vertex or upper most curved feature, in the high rise leg openings, to the waist opening. The vertex in the high rise, leg openings is the intersection of the two side lateral edges of the front and back elastic, or elastic and extensible panels, after they have been bonded together along the seam, and includes in one embodiment, a distinct "pointed" high rise (such as an inverted "V") leg opening portion, as opposed to the continuous circular leg opening of traditional diapers. Alternatively, such high rise, upper leg opening feature is in the shape of an inverted "U". Such bond seams are in one embodiment, generally perpendicular to the relatively horizontal waist edge (or waist band) of the article and extend from the apex of the vertex to the waist edge (as opposed to from some other location along the rising vertex, such as a side of the vertex below the highest point). The waist edge or waist band as the case may be, is in one embodiment, generally aligned or parallel with the transverse direction of the article. As a result of the alignment of the extensible/elastic panel bond seams with the apex of the vertices of non-circular leg openings at a position inwardly from the lateral-most article side edges, a more comfortable, underwear-like article is produced, with greater flexibility for movement of the legs at a user's thigh regions without rubbing against the leg openings. Such invention may also be applied to refastenable absorbent articles so as to provide easy access along the front surface of an article to reclosure mechanisms, while providing targeted elastic or extensible functionality to both the front and back panels of an absorbent garment.

Figure 3A:
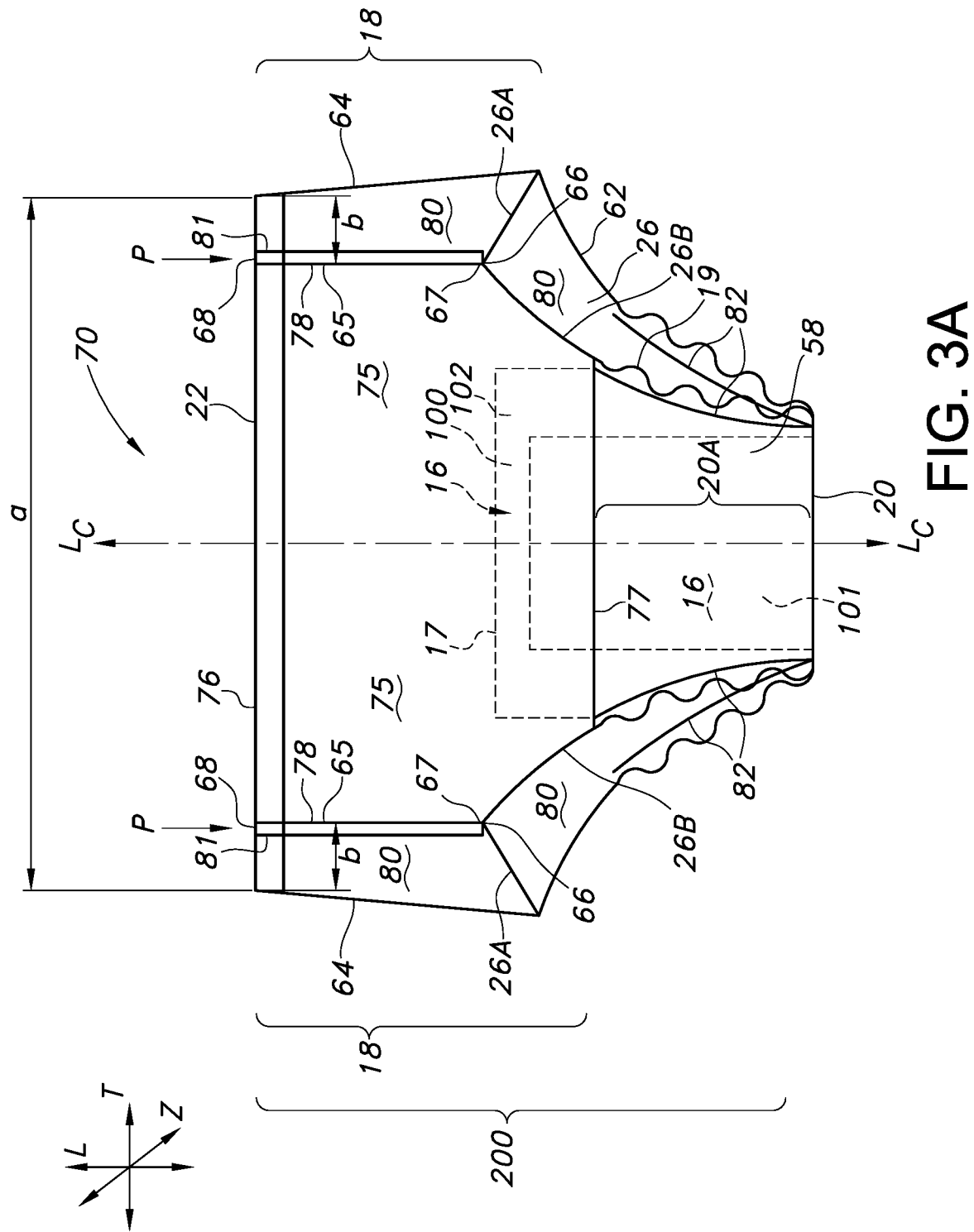
FIG. 3A is a front surface, perspective view of an absorbent article in the form of an incontinence pant, in accordance with the invention.

As can be seen in the embodiment of FIG. 3A, a front surface, perspective view of an absorbent article in accordance with the invention is shown (in the form of an incontinence pant) 70. The illustrated absorbent article 70 is in a relaxed and flattened state. The absorbent article 70, includes a longitudinal direction L, a central longitudinal direction Lc, a transverse direction T ending in lateral-most transverse direction side edges 64, and a depth direction Z. The absorbent article has an interior space (not shown except in leg openings) defined by the interior surfaces of the article (the interior surfaces to be in contact with the user when the absorbent article is in use) and exterior surfaces, that may have contact with an outer garment of a user when the absorbent article is in use. Such exterior surfaces in any event, will face away from the user when the absorbent article is in use. The incontinence pant 70 is generally symmetrical about the central longitudinal direction Lc and includes a waist edge (and in this embodiment a waist band) 22 defining a waist opening (not shown). The incontinence pant 70 further includes two leg openings 26. The waist and leg openings lead to the interior space of the absorbent article 70. The two leg openings 26 are symmetrically positioned on each side of the central longitudinal direction Lc on the front surface 200. As seen in the figure in the front surface view, the leg openings are situated such that two leg opening edges 26A (from a back extensible or elastic panel 80) and 26B (from a front elastic panel 75) defining the leg openings, intersect forming a vertex 66 adjacent to, but not at each lateral-most side edge 64 of the absorbent article 70. In the article, the vertices 66 are not situated on the lateral-most side edges 64 themselves, but instead are positioned inwardly (or forwardly) from the lateral-most side edges 64 desirably on the front surface, towards the central longitudinal direction Lc. It should be noted that such panel edges may lead to a point as illustrated, such as in an inverted "V", or alternatively, to an inverted "U"-shaped feature. In either event, the term "vertex" is meant to describe an elongated edge feature of a high rise leg opening, that is, a feature that includes an elongated shape leading to a "highest point" on the leg opening edge, as opposed to the highest point on a circular edge. The vertices 66 are created as a result of the nonsemi-circular leg cuts made in the front and back elastic and extensible (or elastic) panels, or rather the sheets that are eventually made into the front and back panels (and also in some instances parts of the absorbent insert lateral edges). The shape of the leg cuts/openings are desirably ergonomic in design, such as those described for example in U.S. Pat. No. 7,011,653 to Imsangjan et al. However, unlike the seam and leg opening configurations of the Imsangjan reference, the bond seams 65 of the current application are not to be finally located at the lateral-most side edges of the absorbent article, and do originate at the apex of the vertices and extend to the waist edge 22, as opposed to originating at some lower point along the sides of a vertex-like feature. For example, in the Imsangjan reference, in FIGS. 1, 2, 5, 6, 7, 8, 9, and 10, the side seams are either shown at the lateral-most article side edges or originate at some point below the highest portion of the vertex shown in those figures. For the purposes of this application, the term "bond seam" refers to that structure of connection between the front and back panels by which the panels are fixed together in the absorbent article. Such bond seam may be for example, by adhesive, ultrasonic or thermal bond methods, or a combination thereof. The bond seams 65 and leg openings 26 (including vertices 66) are all visible along the front surface view in the inventive article.

The highest points (referred to as "apex" for the purposes of this disclosure) 67 of the leg opening vertices 66, are aligned with one end of the bond seams 65 which seams are formed by a lateral side edge 78 of the front elastic panel 75, and a lateral side edge 81 of the back extensible or elastic panel 80. The bond seams 65 extend generally along a line on the article longitudinal direction to points 68 on the waist edge 22 (or waist band as the case may be). The points are located at positions "P".

Desirably, in one embodiment, the paths of the bond seams 65 are generally parallel with the longitudinal direction of the absorbent article. In one such embodiment, it is desirable for the bond seams 65 to be perpendicular to the waist edge 22. It is desirable in one embodiment for the waist edge 22 to be parallel with the transverse direction of the absorbent article (generally horizontal). In one embodiment, the bond seams 65 are at a relatively small angle with respect to the lateral most side edges 64 of the article. As noted, the two leg opening 26 edges 26A, 26B form elongated openings 26, in that they are not circular but include a distinct inverted "V-shaped" or "U-shaped" portion directed generally along the article longitudinal direction L.

The bond seams 65 attaching the front 75 and back 80 panels may be flush with the panels (such that no additional material protrudes from either side of the actual bond seams) or may alternatively include additional material that protrudes from either side (interior surface or exterior surface) of the seam of the panels. Such seams may be lap seams for example. Desirably, if there is to be extra material used to form the bond seams 65, it protrudes outwardly from the seam on the absorbent article exterior surface (towards a user's clothing) and not along the interior, user-facing surface of the absorbent article. Such interior facing material might cause unnecessary friction or rubbing during use, even though located inwardly of the absorbent article lateral-most side edges 64. Desirably in one embodiment, the additional material extends between about 4 mm and 15 mm out from the actual bond seam line, and lies against the exterior surface of the extensible or elastic back panel 80, in the direction towards the absorbent article lateral-most side edges 64. In any event, because the bond seams 65 are situated inwardly or forwardlly (closer to the central longitudinal direction) from the absorbent article lateral-most side edges 64, the appearance on the front surface view of the absorbent article is of an article with less prominent seams (not being located along the lateral-most side edges 64 of the absorbent article), and one which creates a visual impression of an article that more closely resembles traditional woven underwear. The bond seams 65 may be permanent (in that they are not designed to be casually opened or ripped without relatively large force being applied thereto) or alternatively, they may be temporary bond seams that are designed to be casually opened. Such temporary bond seams may be utilized so as to accomplish the limited purpose of causing the narrowing of the front panel following bonding, cutting, and relaxation of the article during manufacture, as is explained further below.

The bond seams 65 are located towards the "V-line" region of a user's body. As noted, in a further embodiment, such bond seams 65 may be further positioned on a slight angle with respect to the lateral-most side edge 64 adjacent each bond seam line (as seen in FIG. 3A), desirably angled so as to more closely approach the lateral-most side edge 64 at a location towards the waist edge 22.

In the front surface, perspective view of FIG. 3A, the lateral-most side edges 64 of the inventive absorbent article (following manufacture) are comprised solely of portions of the extensible or elastic back panel 80 material rather than the meeting line of the front and back panels, as in prior-art, garment-like, absorbent articles. Essentially, the back panel 80 wraps around the lateral-most waist regions and extends partly into the viewable front surface 200 of the absorbent article 70 (when in a relaxed and flattened state). This uniform lateral side edge material allows for less friction during use, as a result of the elimination of the traditional inside surface seam rubbing against the lateral-most waist regions of a user's body. The combined impact of an off, lateral-most edge seam and alignment with a leg opening vertex 66 also on the front surface, provides for additional fit/comfort and emotional benefits to the user of such absorbent article. Further, such configuration provides more backside coverage and less material in the flexion point of the legs.

As noted in the illustrated embodiment of FIG. 3A, the absorbent article 70 is shown viewed from the article front surface 200, and such article is in a relaxed and flattened state. That is, such article is shown as it would be viewed when placed in an untensioned configuration on a flat planar surface such as a desk, with the front surface 200 facing the viewer. The absorbent article 70 includes an absorbent core insert (or assembly) 16 that is bonded at least at each absorbent insert opposing longitudinal direction end edge 17 to at least one elastic front panel 75 and at least one extensible or elastic back panel 80. The absorbent core insert 16 includes opposing lateral side edges 19 that extend between the opposing longitudinal direction end edges 17. The elastic front panel 75 includes elastic front panel upper edge 76 (corresponding to the waist edge 22) and elastic front panel lower edge 77. The elastic front panel 75 also includes the noted two lateral, front panel side edges 78. The lateral side edges 81 of the extensible or elastic back panel 80 wrap around the absorbent article lateral-most side edges 64 and are bonded to the elastic front panel 75 lateral side edges 78 at the bond seams 65, which appear in the front surface view. The bonding of the seam lines may be accomplished by a variety of known bonding techniques, but desirably in one embodiment, by ultrasonic bonding.

In the illustrated embodiment, the front elastic panel 75 lower edge 77 does not extend to the lowest edge of the absorbent article 70 along the longitudinal direction. Rather, an extending portion of the absorbent core insert 16 defines the lowest edge 20 of the absorbent article at the crotch region 58. The extending exposed portion 20A of the absorbent core insert 16 extends out from under the front elastic panel 75 lower edge 77, and typically does not itself include elasticity.

The minimum transverse direction (or lateral) width of the absorbent article front surface 200, when in a relaxed and flattened state, and including the cumulative widths of the exposed, front elastic panel 75 and back extensible or elastic panel 80 lateral portions, is shown as "a" in the figures. This minimum transverse direction width "a", is the distance between the absorbent article lateral-most side edges 64 at their narrowest point. As seen in FIG. 3A, the width between the absorbent article lateral-most side edges 64 may be progressively smaller along the lateral-most side edges 64, traveling from the top of the leg openings 26 to the waist edge 22. Alternatively, the width between the lateral-most side edges 64 may be of consistent lateral dimension (not shown) along the full length of absorbent article lateral-most side edges 64. In one embodiment, the minimum transverse direction width "a" of an article in a relaxed and flattened state, is desirably between about 200 mm to about 500 mm, especially for adult care products. In a second embodiment, the minimum transverse direction width "a" of an article in a relaxed and flattened state is desirably between about 70 mm to about 200 mm, alternatively, between about 110 mm to about 170 mm, especially for baby and child care products.

The discrete width of the extensible or elastic back panel 80 portion that is exposed about each lateral-most side edge of the absorbent article 70 on the front surface view (in the relaxed and flattened state), is noted as "b". In one embodiment, it is desirable for the transverse direction width "b" of the exposed back panel 80 on the front surface 200 at the waist edge, to be between about 5 mm to 125 mm, alternatively, between about 10 mm to 113 mm, especially for adult care products. It should be noted that there are two "b" widths on the front surface 200, one adjacent each lateral-most side edge 64. In a second embodiment, it is desirable for the transverse direction width "b" of the exposed back panel to be between about 2 mm to about 50 mm, alternatively between about 16 mm to about 25 mm, especially for baby and child care products. This distance "b" is the narrowest distance measured from a lateral-most side edge 64 to the closest bond seam 65. It has been determined that a favorable relationship exists between the dimensions "a" and "b" such as can be described by the equation, b=(a*(5% to 50%))/2), alternatively, b=(a*(10% to 45%))/2). It should be appreciated that the position of the bond seams 65 are desirably each anteriorly shifted forward towards the central longitudinal direction (such that they are each visible on the front surface) by the distance "b" so as to both improve an article's resemblance to undergarments and also to improve a user's comfort and fit, based on better backside coverage and less material in the flexion of the leg. In this fashion the bond seams are moved from the traditional positions near the sides of the user's legs, to a position closer to the inner thigh. It has been found that a position that is less than about 2.5% off of the lateral-most side edge, or greater than about 25% off of the lateral-most side edge would fall outside the region of a user's upper thigh and negatively result in an article without an underwear-like appearance and with less comfort and fit (as a result of less flexibility of movement of a user's thigh without rubbing or friction with the leg opening peripheral edge). The inwardly situated bond seams 65 (inwardly with respect to the absorbent article lateral-most side edges 64 and more towards the central longitudinal direction Lc) are desirably positioned at position "P" along the waist edge 22 (or reference number 68).

The absorbent core insert 16 (or assembly) in the illustrated embodiment of FIG. 3A, includes at least a liquid permeable user-facing topsheet layer 100, a liquid impermeable garment-facing backsheet layer 102, and a sandwiched absorbent core layer 101, that is sandwiched between the topsheet layer 100 and the backsheet layer 102. As shown in FIG. 3A, the dimensions of the topsheet layer 100 and backsheet layer 102 are desirably the same in the longitudinal and transverse directions, although in an alternative embodiment, the topsheet layer 100 dimensions may be shorter and/or narrower than those of the backsheet layer 102. The topsheet layer 100 and backsheet layer 102 are desirably of the same dimensions and sealed at their edges, with both extending beyond the dimensions of the absorbent core layer 101 in the longitudinal and transverse directions. While such absorbent core insert 16 is shown partly exposed 20A from under the front elastic panel 75 in the crotch region 58 of the absorbent article 70, such elastic front panel 75 may instead completely cover the absorbent insert (not shown) in a further embodiment. Wherever such covers the absorbent core insert, it may alternatively include elastically deadened regions that overlap or are adjacent to the absorbent core insert in the article depth direction Z.

The elastic front, and elastic or extensible back panels 75, 80 are bonded together to form the waist region 18 (defining the waist opening). The waist region 18 is designed to encircle the lower abdominal region of a user as well as to sit longitudinally above/adjacent the crotch area 58 of a user. The waist region includes the lateral edges which define the lateral-most side edges 64 of the absorbent article along the transverse direction. Optionally, the absorbent article will also include a waist band, which may be integral with the panels 75, 80, or of a separate piece construction which is attached to the panel upper edges 76. Further, the absorbent article 70 can include leg opening 26 elastic elements 82 which at least partially encircle the leg openings 26 to maintain the tension of the leg openings 26 around a user's legs (upper thighs) during use. Such elastic elements 82 may be formed of any known elastic stranded materials, elastic films or ribbons, or laminates of such.

Figure 3C:
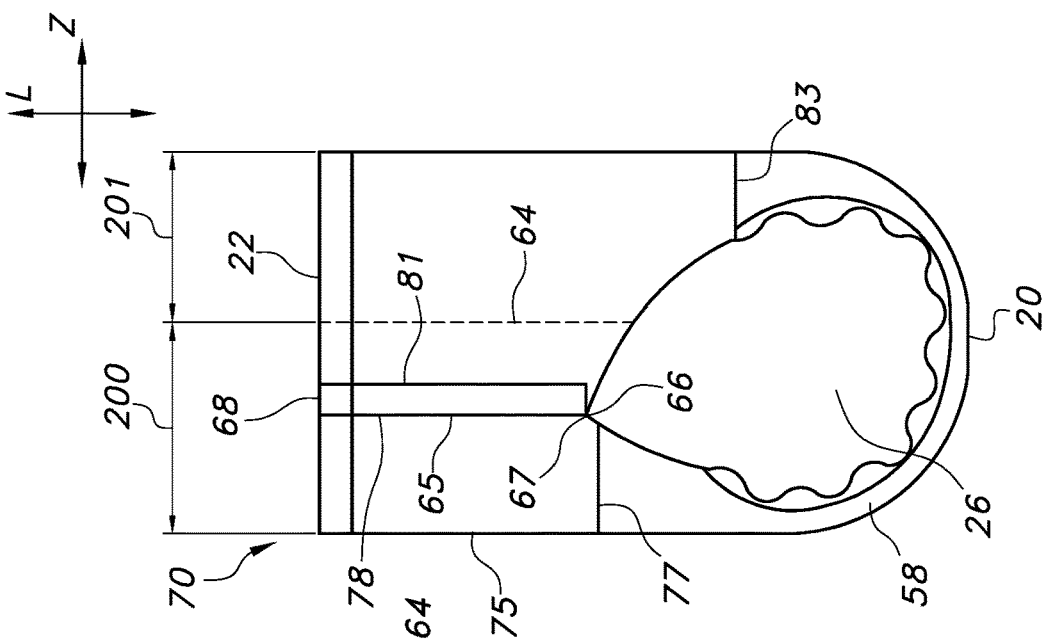
FIG. 3C is a side perspective view of the absorbent article of FIG. 3A.
Figure 3B:
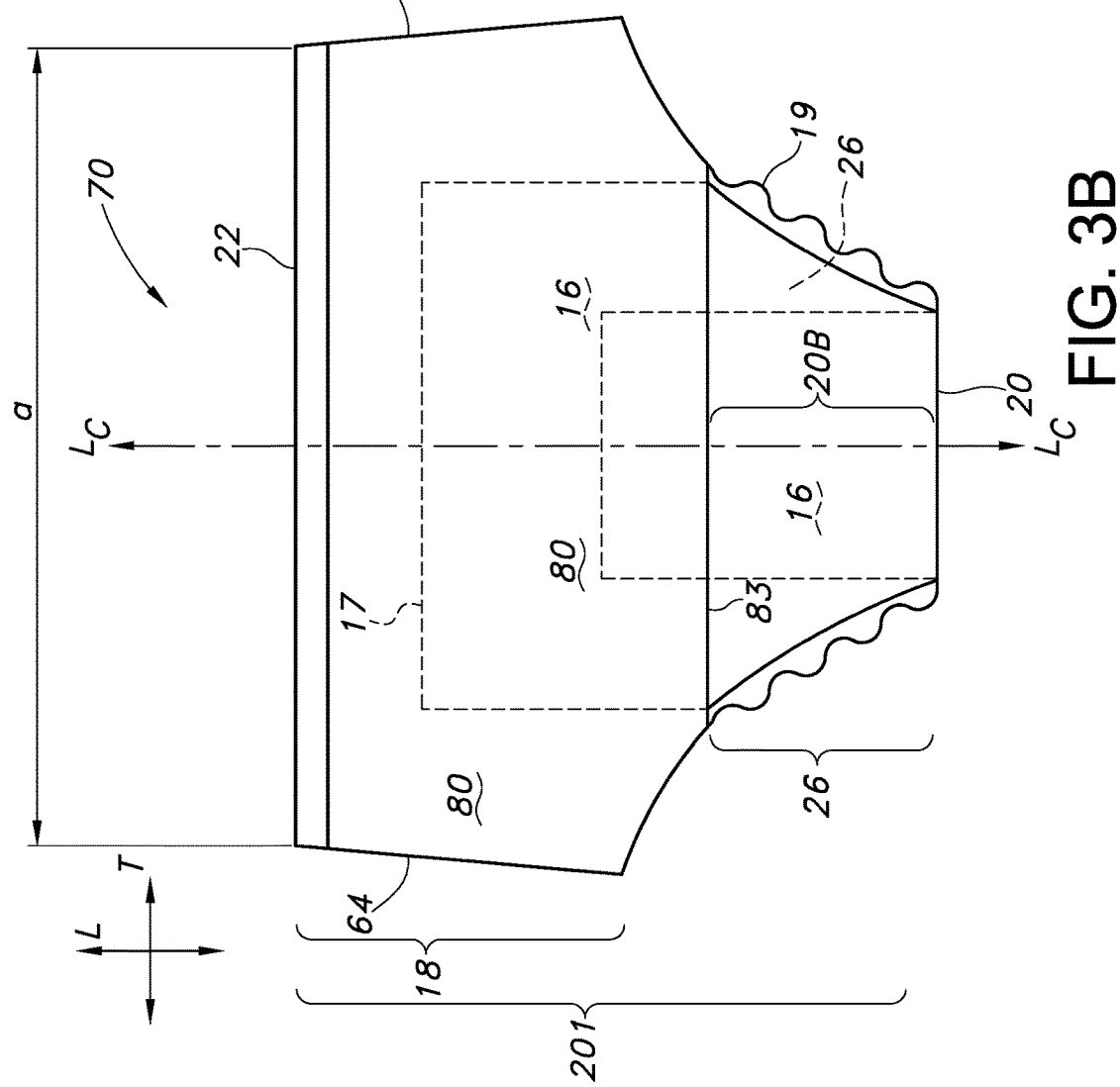
FIG. 3B is a back surface, perspective view of the absorbent article of FIG. 3A.

FIG. 3B illustrates the back surface, perspective view of the incontinence pant 70 of FIG. 3A in a relaxed and flattened state. As can be seen in the figure, the back extensible or elastic panel 80 extends across substantially most of the back surface 201 of the incontinence pant 70. It includes a back panel lower edge 83 which covers much of the absorbent core insert 16. Less of the absorbent core insert 16 is visible (in one desirable embodiment) along the back surface 20B than along the front surface 20A. In the desirable embodiment in which the front panel is narrower than the back panel, none of the front elastic panel 75 is visible from the back surface view. Neither are the actual openings of the leg openings 26 visible from the back surface view. The bond seams 65 are similarly not visible from the back surface view of the finished article.

FIG. 3C illustrates a side perspective view of the final/post production incontinence pant 70 of FIG. 3A. As can be seen in the figure, the bond seams 65 are positioned away from the absorbent article lateral-most side edges shown in phantom 64. They are illustrated as positioned forward from the lateral-most side edges 64, towards the article central longitudinal direction (and along the front surface 200). The lower edge of the back elastic or extensible panel 83 extends lower along the absorbent article longitudinal direction L (on the back surface 201) than the front elastic panel lower edge 77. The bond seam 65 is aligned with the leg opening 26 vertex 66, and in particular, the apex 67 of the vertex on the front surface 200, and both are situated forward of the absorbent article lateral-most side edge 64. The front surface view 200 can be described as illustrating structures to the left of the in-phantom, lateral-most edge 64 of FIG. 3C. The back surface view 201 can be described as illustrating structures to the right of the in-phantom, lateral-most edge 64 of FIG. 3C.

As will be described further below in connection with the manufacturing steps of such absorbent articles, upon the absorbent article 70 manufacture under the desired levels of tension (or machine draw), and following folding, bonding, and cutting of leg openings and the individual absorbent articles from base sheets making the front and back panels, the individual absorbent articles are allowed to retract. This retraction of the respective sheets (and resulting panels) causes a rotation of the bond seams 65 from their original, in-formation, lateral-most edge position (as seen in FIG. 4B), to a final, post-production front surface position as shown in FIG. 4E, and also as in FIG. 3C. Essentially, during initial manufacturing steps, the position of the bond seams 65 start out at the lateral-most side edge, but upon severance from the base sheets and article retraction, they move or rotate forwardly or rearwardly as desired, from the lateral-most side edge to a position closer to the central longitudinal direction. Therefore in one preferred embodiment, during manufacture, the bond seams 65 shift from the lateral-most side edge, towards the central longitudinal direction on the front surface, thereby creating a new lateral-most side edge 64 as shown in FIG. 3C that is free of a bond seam. Desirably, the bond seams rotate anteriorly as the elastic materials in the absorbent article are permitted to retract. Therefore, during manufacture the transverse direction width dimensions of the front and back panels start out the same, and then finish with the front panel being narrower than the back panel along the absorbent article transverse direction, accounting for the rotation of the bond seams 65 forwardly to the front surface position.

Figure 3D:
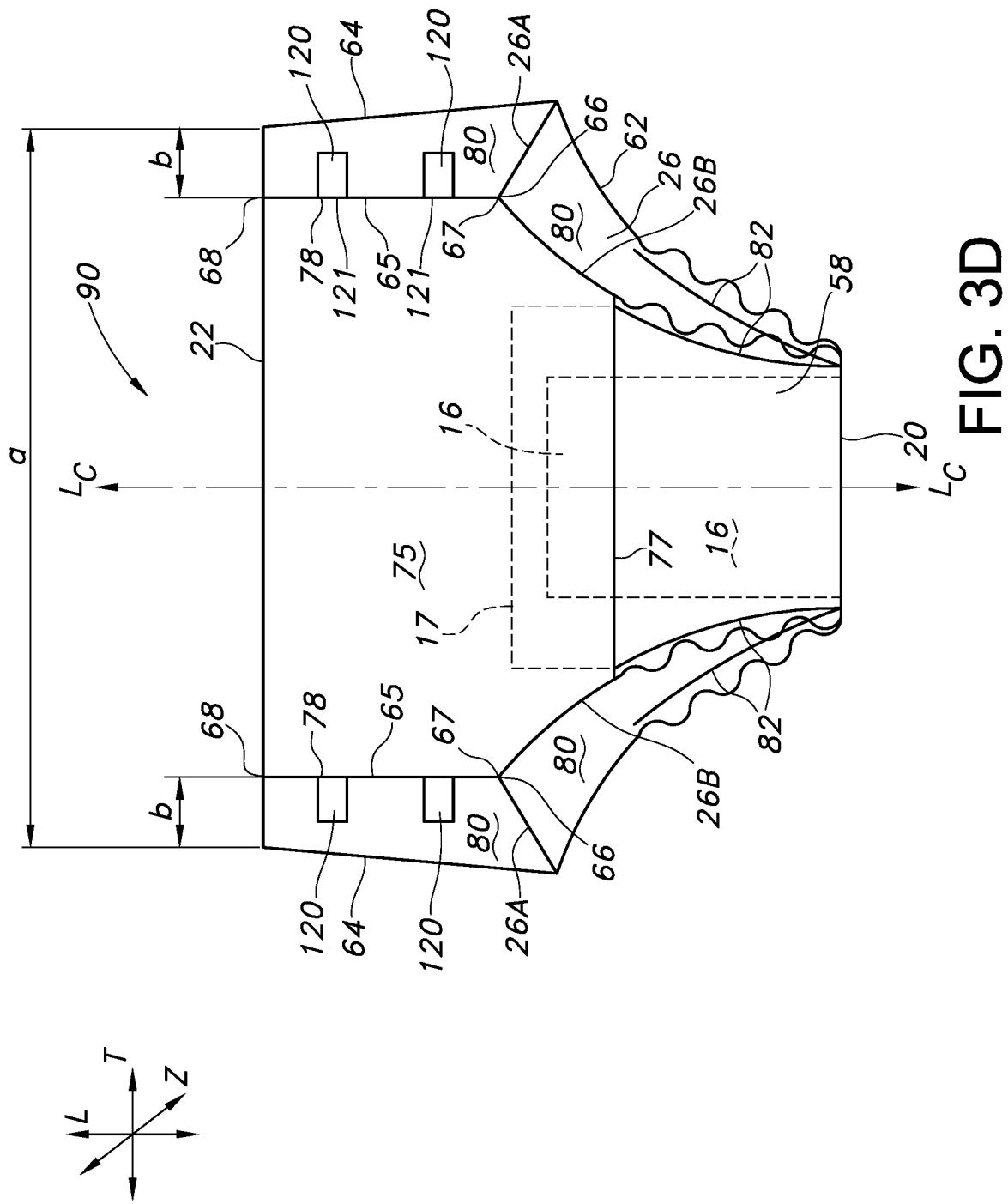
FIG. 3D is a front surface, perspective view of an alternative embodiment of a refastenable absorbent article, in the form of an incontinence pant in accordance with the invention.

FIG. 3D illustrates an alternative embodiment of an incontinence article 90 in accordance with the invention. In the particular embodiment of FIG. 3D, a refastenable absorbent article is illustrated in the fastened state. While the absorbent article 90 includes similar structures as those previously described in earlier embodiments, it also includes fastening components 120 which may be of any of the known types of fastening components available for absorbent articles. Such fastening components 120 may be in lieu of a permanent bond seam, or in addition to a bond seam 65 (such as a temporary bond seam). Such fastening components include adhesive tapes or "hook-and-loop" style fasteners, or a combination of each. In the illustration, two sets of rectangularly-shaped fastening components are shown attached to each lateral side edge of the front elastic panel 75 (on the front surface). While shown attached to an edge, such fastening components may be offset from such edge in an alternative embodiment, and presented to a user originally in an unfastened condition. Such fastening components are attached to a mated component or material situated on the back panel 80. For example, if such fastening component is an adhesive tape, it is desirably fastened to a film material on the back panel. If such fastening component is a hook material, it is fastened to a loop material on the back panel (such as a nonwoven material) or vice versa. It should be appreciated that the placement of such fastening components 120 can be reversed between the front and back panels. Such fastening components can be of any desirable shape, such as geometric or abstract shapes. Further they can be of any desirable dimension and may be present in any desirable number along the lateral side edges of the panels. For example, such fastening components may instead be formed from an elongated single component that runs substantially the full length of the panel lateral side edges (such as greater than 50% of the length) or less than substantially the full length. No matter what the placement, it is important in one embodiment, for either the line of secured edges 121 of the fastening components (as the case may be in this embodiment) or the line of fastening components 120 themselves, to be positioned in alignment with the highest point 67 of the leg opening vertex 66 and inwardly of the lateral-most side edge 64 of the absorbent article for increased user comfort, ease of re-closure, and emotional preference. Such fastening components 120 are desirably all visible on the front surface view following rotation of the back panel lateral edges to an asymmetric configuration. The refastenable, fastenable components 120 are in this embodiment shifted forward to the front surface over the course of manufacture, as would the previously described side bond seam rotates more towards the front surface 200 upon relaxation of the article. Therefore, in the previously described fully bonded, absorbent article embodiment (not refastenable product) the side bond seams move anteriorly upon retraction, such that they are no longer "side" bond seams. In a similar fashion, in the refastenable embodiment of the absorbent article, the refastenable components 120 are attached to the article at a similar location as the initially described side bond seams and then move as a unit towards the front surface (or back surface as the case may be) upon panel retraction. In one embodiment, such panels are attached via a temporary bond seam or element, such as a relatively weaker bond seam or frangible bond seam, but also include refastenable components attached to their surfaces, either along the panel lateral side edges or adjacent thereto. See in this regard U.S. Pat. No. 7,156,833 to Couture-Dorschner et al. for a description of temporary or frangible side bond seams, which is incorporated by reference thereto in its entirety. In still a further alternative embodiment, such moveable side bond seam includes a line of perforation adjacent to the seam, or other tearable mechanism/line of weakness adjacent to the bond seam, to allow the bonded article to be easily removed.

A stylized example of a method of manufacturing an absorbent article in accordance with the invention is illustrated in FIG. 4. In particular, a sequence of manufacturing steps can be seen in FIGS. 4A-4F. As can be seen in FIG. 4A, the line of production of articles includes at first the production of a series of absorbent article blanks using two running parallel sheets 250, 251. Such sheets are continuous initially and will eventually form the elastic front panels 75 and the elastic or extensible back panels 80 on a series of absorbent articles. The sheet materials are shown traveling from left to right in the figure along the transverse direction of the article blanks. In early stages of the process, no distinct waist, lateral side edges are present. Such will form upon bonding and cutting steps later in the process. Therefore the eventual sheet lateral side edges are shown in phantom as 78, 81. In the illustrated embodiment, the elastic sheet 250 that will eventually form the front elastic panel 75 is maintained under higher tension t3 (represented by larger arrow 48) than the lower tension t4 (represented by smaller arrow 49) of sheet 251, that will eventually become the back panel 80. Absorbent inserts 16 will be bonded to the material sheets 250, 251 at the absorbent insert opposing longitudinal direction ends 17, and generally in positions perpendicular to the sheet directions of stretch, while the sheets are maintained under their respective tensions. The front elastic panel 75 and back at least extensible, or elastic panel 80, will have the same lateral widths along the absorbent article blank transverse direction T during the production process, until individual article separation. The front and back panels may or may not be produced of the same materials. For example, in one embodiment, such are produced from the same materials, such as elastic sheets having the same elastic properties/functionality. In an alternative embodiment, such are produced from two different materials, such as two materials, each having different retractive power/force. For example, such front panel sheet may be produced from a material having a higher level of retractive power/force than the back panel sheet. In such an alternative embodiment, the tensions applied to such sheets during the manufacturing process may be the same (not shown), but the differences in retractive power between the sheets will result in an asymmetric product upon, bonding, cutting and relaxation.

Prior to absorbent article 70 production, the first sheet of an elastic material 250 having a longitudinal direction and a transverse direction with the sheet being elastic in the transverse direction, is produced either offline or inline and placed on the article production machine. Concurrently, the second sheet of at least an extensible material (but desirably also an elastic material) 251 having a longitudinal and transverse direction, and being either extensible or elastic in at least the transverse direction, is also produced offline or inline and placed on the production machine in parallel with the first sheet, such that the sheet transverse directions travel in tandem on the production machine along their transverse directions. The sheets are exposed to the desired tensions along the transverse direction.

The elongated and ergonomic leg openings 27 are cut from the first and second sheets 250, 251, with a leg cut shape that will result in an elongated leg opening having a distinct vertex along one side edge (the upper edge portion of the leg openings 26, along the absorbent article longitudinal direction). The actual cutting step can occur either prior to bringing the sheets in an overlaying configuration or following such step (e.g. folding step). As seen in FIG. 4B, either one of the sheet materials is then folded 91 about the other along fold line 140. For example, in one embodiment, the elastic material first sheet 250 is folded 91 (as seen in FIG. 4A) about the fold line 140 over the second sheet of either elastic or extensible material 251 to form a folded absorbent article blank(s) (not yet a finished and separated absorbent article), such that the outer waist edges 22, 23 of the two sheets are aligned (and the sheets overlap completely). Alternatively, the extensible sheet may be folded about the elastic sheet. The bond seams 65 are then created using traditional bonding methods, with the seams desirably aligned with the leg opening formed-vertices 66, and extending to the outer edges of the two sheets 22, 23 (which will eventually form the waist edge). At this point in the production method as seen in FIG. 4B, the lateral widths between bond seams of the first and second sheets for each absorbent article blank are the same as illustrated by W3 and W4. The absorbent article blanks are cut along cut lines 92 adjacent to, and desirably at a position centered between the bond seams 65 (laterally outward from the bond seams). It should be understood that the step of cutting 92 the articles, may occur either after the creation of bond seams 65, or concurrently with the creation of bond seams 65. The now formed and separated individual articles 70 are then allowed to retract, such that the higher tension that had been placed on the elastic material first sheet 250 causes the differential retraction of the first sheet (now front elastic panel 75) relative to the second sheet 251.

As can be seen in FIG. 4C, the retraction results in the rotation (shown by arrows) of the created side bond seams 65 from their original position at the lateral-most side edge to a second position on the front surface 200 of the absorbent article, thereby creating front surface bond seams 65 that extend from the apex of the leg opening vertices 66 to the waist edge 22 along the front surface 200 of the absorbent article. A new lateral-most side edge 64 is formed following the retraction. This is further illustrated in FIGS. 4D-1 and 4D-2, which show a stylized top view of an open absorbent article (looking into the interior space through the waist opening) before and after retraction. As can be seen in the Figures, the position of the bond seams 65 shift to the front surface following the retraction illustrated from FIG. 4D-1 to 4D-2.

During the retraction of the front panel 75 as a result of the removal of applied tension along the transverse direction on the elastic sheet 250 (or front elastic panel 75), the liquid impermeable backsheet transverse dimensions may also experience shrinkage as the overall front panel 75 retracts along the transverse direction, such that the lateral width dimension of the front panel, liquid impermeable backsheet edge 17 narrows with respect to the lateral width dimension of the back panel, liquid impermeable backsheet edge 17'. Such is stylistically illustrated in the open absorbent article 70 of FIG. 4F. While such open absorbent article 70 never appears in the actual process as it is shown in FIG. 4F, it is illustrated for the ease of understanding that the transverse width dimension of the elastic front panel 75, W3' has reduced in size from the original dimension W3 and from the back panel dimension W4', that it originally had during the earlier steps of the process (prior to cutting into discrete articles, and prior to retraction). Before retraction of the elastic panel the transverse direction widths W3, W4 of the two panels are the same. Following folding, bonding and cutting, the transverse direction widths W3' and W4' are different as a result of the differential tension that was applied to the two sheet materials (or alternatively, the differential retractive properties of the first and second sheets employed during the manufacturing process). Such differential elastic sheets may be employed in combination with differential tensions on the sheets in an alternative embodiment.

In one embodiment, the applied tension (or machine draw) along the transverse direction of the elastic sheet material of the front panel is between about 1× and 2× of the applied tension along the elastic sheet material of the back panel. Alternatively, the applied tension (or machine draw) along the transverse direction of the elastic sheet material of the front panel is between about 1.3× and 1.6× of the applied tension along the elastic sheet material of the back panel. Such is desirable for two sheets having the originally the same level of elasticity. In one embodiment, the fully retracted length of the front elastic panel is shorter than the fully retracted length of the back elastic panel.

In a further embodiment, an alternative process for creating a refastenable absorbent article is also contemplated. In such an embodiment, it is desirable for the permanent bond seam 65 to be replaced with a temporary or frangible bond seam. In yet a further alternative embodiment, such permanent bond seam is replaced with a temporary or frangible bond seam and separate fastening components are also attached to the article front and back panels. As with the previous embodiments, once the absorbent article is cut from the blank, and a discrete absorbent article is formed, it is allowed to retract, thereby moving the temporary bond seam and refastenable components if present, which are aligned along a line from the vertex to the waist, to also rotate/forwardly towards the absorbent article central longitudinal direction, and end in a final position along the absorbent article front surface (as with the permanent bond seam of the prior embodiments). For refastenable absorbent articles, there is an overall expectation of less rotation of the side seams to the front surface if the fastening components are engaged with the front elastic panel. This is the result of the impact of the fastening components on panel material when in the fastened condition, causing the front panel to retract less than in previously described embodiments.

In yet another alternative method of manufacture of the absorbent articles in accordance with the invention, the sheet materials which will eventually form the front and back panels of an absorbent article are each (a) stretched under tension along their transverse directions to a desired extent, such that one sheet material is under greater tension than the other, (b) an absorbent assembly is then contemporaneously bonded to the two sheet materials, perpendicular to the sheet materials' direction of stretch, while the sheets are in their respective stretched condition, (c) leg holes are then respectively cut from each of the two stretched sheet materials, which such leg holes each including a vertex feature, (d) the sheet materials are then overlaid, one over the other, such as about a fold line, (e) the two sheet materials are then bonded at seam lines aligned with vertices to form bond seams at their lateral most side edges, (f) cuts are made laterally beyond their bond seam lines forming individual absorbent articles and, (g) the formed absorbent articles are then allowed to retract, thereby moving the lateral-most side edge bond seams and leg opening vertices to either a front or back surface of the formed absorbent article.

In still another alternative method of manufacture of the absorbent articles in accordance with the invention, (a) the sheet materials that will eventually make up the front and back panels of an absorbent article are stretched along their transverse directions so that one sheet material is under greater tension than the other, (b) the sheets are cut so as to include leg holes with vertices for later alignment with side bond seams, (c) an absorbent assembly is cut to an appropriate shape and bonded to the respective sheet materials in a direction perpendicular to the direction of stretch of the sheet materials, (d) the sheet materials are folded one over the other, (e) bonded at side seams in a position aligned with the vertices, and cut laterally beyond the bond seams to form at least one absorbent article, (f) which at least one absorbent article is allowed to retract such that the bond seams and vertices move to either the front or back surface of the at least one formed absorbent article.

In still another alternative embodiment, (a) the sheet materials that will eventually make up the front and back panels of an absorbent article are stretched along their transverse directions so that one sheet material is under greater tension than the other, (b) an absorbent assembly is cut to an appropriate shape and bonded to the respective sheet materials in a direction perpendicular to the direction of stretch of the sheet materials, (c) the sheet materials are folded one over the other, (d) leg hole cuts are made in the respective sheet materials, such leg hole cuts including vertices, (e) the sheet materials are bonded at side seams in a position aligned with the vertices, and cut laterally beyond the bond seams to form at least one absorbent article, (f) the at least one absorbent article is allowed to retract such that the bond seams and vertices move to either the front or back surface of the at least one formed absorbent article.

In still another alternative method of manufacture, a method of manufacturing a fastened absorbent article 70 having a longitudinal direction, a transverse direction, and a central longitudinal direction includes the steps of a) providing an absorbent article 70 having a front 75 and back panel 80 of elastic materials, the front and back panel being indirectly connected to each other via an absorbent insert 16, the front 75 and back panels 80 each having equal starting transverse direction widths W3, W4 ending in lateral side edges 78, 81 and leg hole cut-outs having distinct vertex portions along their side edges; b) applying unequal tensions 46, 47 upon the front 75 and back 80 panels such that during absorbent article manufacture, the front 75 and back 80 panels are extended along the article transverse direction and allowed to retract to different levels resulting in final front and back panel transverse direction widths, whereby the front panel 75 retracts to a final transverse direction width W3' that is narrower than its starting transverse direction width W3, and also narrower than the starting and final back panel transverse direction widths W4, W4'; c) folding either the front or back panel over the other panel about a fold line 140; d) bonding the front panel to the back panel at the lateral side edges such as to form bond seams 65, and e) cutting the absorbent article at a location outwardly from the bond seams and allowing the absorbent article to relax, whereby a fastened absorbent article is formed having absorbent article lateral-most side edges 64, a waist opening including a waist edge 22, and two leg openings 26 each having a vertex 66, such that the bond seams 65 are separated from the absorbent article lateral-most side edges 64 and whereby the bond seams rotate inwardly towards the absorbent article central longitudinal direction such as to appear on the absorbent article front surface, and extend from vertices 66 in the leg openings (and in particular the apex 67 of each vertex 66) to the waist edge 22.

Alternatively in the method, the waist edge 22 is generally horizontal (aligned/parallel with the absorbent article transverse direction) and the bond seams 65 are generally perpendicular to the waist edge 22. Still in a further alternative embodiment, the bond seams 65 rotate from an initial position at the absorbent article lateral-most edge during production and when the elastic front panel is under tension, to a final relaxed position on the front surface at a location between about 5 mm and 125 mm away from the absorbent article newly created lateral-most side edges 64, alternatively between about 10 mm and 113 mm away from the absorbent article newly created lateral-most side edges 64.

In yet another alternative embodiment of a manufacturing method, the method includes the steps of a) producing a front panel 75 of an elastic material having elasticity along a transverse direction, b) producing a back panel 80 of an extensible or elastic material of a different level of extensibility/elasticity along a transverse direction than the front panel 75; c) producing an absorbent core insert 16 for attachment to the front 75 and back 80 panels in a direction perpendicular to the transverse direction elasticity/extensibility of the front and back panels, the absorbent core insert including opposing longitudinal direction ends; d) bonding the front panel 75 and back panel 80 to the absorbent core insert 16 at the opposing longitudinal direction ends, e) cutting leg openings in the panels f) bonding the front panel 75 to the back panel 80 at side bond seams thereby forming a fastened absorbent article having a transverse direction, a longitudinal direction, a central longitudinal direction, a waist opening having a waist edge 22 ending at absorbent article lateral-most side edges 64, and leg openings 26 each defining a vertex 66; the waist edge 22 having a minimum transverse direction width and whereby the front panel 75 is bonded to the back panel 80 at bond seams 65 positioned inward of the absorbent article lateral-most side edges 64 towards the absorbent article central longitudinal direction Lc and upon a front surface of the absorbent article, the bond seams extending between each of vertices 66 of the leg openings 26 to the waist edge 22, such that the distance "b" between the bond seams 65 and the lateral-most side edges 64 is between 5% and 50%, alternatively between 10% and 45% of the minimum transverse direction width "a"/2 of the absorbent article waist edge when the absorbent article 70 is measured in a relaxed and flattened state condition.

In still another alternative embodiment, the front 75 elastic and back elastic 80 panels are of the same material that have been exposed to different levels of tension (front panel exposed to greater tension) during absorbent article manufacture. In yet another alternative embodiment, the front 75 and back 80 panels of elastic material are of different materials, each demonstrating different level of elasticity/extensibility. Such different materials may also be exposed to different levels of tension during article production, such as the front panel is exposed to greater tension. It should be recognized that in a desirable embodiment both panels are elastic or demonstrate different levels of elasticity (with both having at least some elasticity). In either event, following relaxation (and retraction) of the front panel as a result of the article being formed, bonded and cut, the front panel experiences a reduction in transverse direction width such that the bond seams and leg openings with vertices, are aligned and positioned along the absorbent article front surface when in a relaxed, flattened configuration.

In yet still a further alternative embodiment of the production method, the waist edge 22 is generally horizontal and aligned with the absorbent article transverse direction. In a further alternative embodiment, the bond seams 65 are either perpendicular to the waist edge 22, or at a slight angle with respect to the lateral-most edges 64. In still another alternative embodiment, the front elastic panel retracts 25% of its transverse direction width and the back elastic panel retracts 10% of its transverse direction width during the process of absorbent article manufacture.

It should therefore be understood that in many of the above described embodiments, the front elastic panel 75 is exposed to higher levels of article transverse direction stretch/tension 46 than the back extensible or elastic panel 80 during the production process, such that it retracts to a different extent (a greater extent) upon relaxation than the back extensible panel 80, desirably such that its final after production width shrinks from the starting width W3 to the finished width W3'. The resulting width of the front elastic panel 75 at the end of production is reduced with respect to both its starting width W3 and the width of the back extensible panel W4, W4'. After the absorbent article blank is folded about fold line 140 (or the two front and back panels are brought together), the bond seam is added to attach the front and back panels to each other and the discrete articles are cut from the sheets. The bond seams 65 following retraction, end up positioned inward of the absorbent article lateral-most side edge 64 and aligned with the apex 67 of the vertices 66 in the leg openings 26. Following retraction and rotation of the bond seams 65, the front and back panels become asymmetrical in appearance (as a result of their altered retracted dimensions).

In yet still another alternative embodiment of the invention, the front and back elastic panels are produced from two different materials under the same tension and machine draw, but which materials demonstrate different levels of retraction along their transverse direction due to their differential retractive powers or force. Such differential retractive power may be attributed to either different basis weights, different thread elongations (if of a thread or strand material), or different polymer blends in the elastic film or strand component of the panel material.

In another alternative embodiment, elastic laminate materials of both panels are processed under the same tension or machine draw. The panels are of the same length under this applied tension. However, the materials of the respective panels differ in the retractive force inherent in their manufacture (due to differences in polymer blend or basis weight of elastomer). In particular, such differential in retractive force is present whether such elastic material is of a single layer elastic material or a multiple layer elastic laminate, such as a stretch-bonded laminate having a central elastic core layer covered with one or more inelastic sheets. When the manufacturing tension is released during this alternative process, the panel with the greater retractive force retracts to a shorter length and demonstrates the desired reduced dimension, such that an asymmetric article is produced with bond seams and leg opening vertices aligned on the front surface of the article. Such differential retraction may be accomplished in this alternative process by use of a stranded laminate composition in which the front panel includes relatively higher decitex elastic strands at a particular density of threads per inch, and the back panel includes relatively lower decitex elastic strands at the same density of threads per inch. While both panels in such alternative process are processed at a similar elongation with a high tension in the final laminate due to the tension in the supporting nonwoven cover materials (spunbond for example), the difference in retractive power, provided by the increased basis weight of the front panel threads results in the seam and vertex rotation specified in the invention.

Generally, a multi-panel absorbent article in which front and back elastic panels 75, 80 are indirectly connected via an absorbent core insert or assembly, is described in U.S. Pat. No. 7,604,624 to Veith et al. which is hereby incorporated by reference thereto in its entirety to the extent it is not inconsistent herewith. As previously noted, at least one liquid permeable topsheet layer, at least one absorbent core layer, and at least one liquid impermeable backsheet layer is also to be included in such article.

The front elastic panel 75, and back elastic or extensible panels 80 which are the outer stretchable layers described herein, are desirably in one embodiment, both elastic, alternatively in another embodiment one elastic panel (front panel) and one extensible panel (back panel). If both panels are elastic, they can be of the same material or the same level of extensibility/elasticity, or of different materials or different levels of extensibility/elasticity. The panels be constructed from various materials known in the art so long as such are placed in the absorbent article in a fashion that they can be being stretched along the desired article transverse direction. Desirably, in one embodiment, such front and back elastic panels (or outerlayers) are breathable so as to provide additional comfort for users of the absorbent article.

One suitable material for use as the elastic front and back panels is a stretch-bonded laminate (SBL) in which an elastic core or middle layer is elongated before two opposing outer nonwoven layers are attached thereto. Another suitable material for the front and back extensible/elastic panels is a necked bonded laminate (NBL). The NBL material is also a three-layer laminate but the elastic core or middle layer is not pre-stretched prior to being attached to the two outer nonwoven layers. Instead, the opposing outer layers are necked stretched before the elastic core or middle layer is attached to them Other examples of such elastomeric materials that can be used for the front and back panels include a continuous filament stretch bonded laminate (CFSBL), a vertical filament laminate (VFL), a necked stretch bonded laminate (NSBL) or a necked thermal laminate (NTL). Combinations of the above materials can also be used. Such materials are described in U.S. Pat. No. 4,720,415 to Vander Wielen et al., U.S. Pat. No. 5,366,793 to Fitts et al., U.S. Pat. No. 5,385,775 to Wright, U.S. Pat. No. 6,969,441 to Welch et al., U.S. Pat. No. 6,978,486 to Zhou et al., U.S. Pat. No. 7,803,244 to Siqueira et al., and U.S. Pat. No. 5,226,992 to Morman et al., each of which are hereby incorporated by reference thereto in its entirety. The nonwoven laminates will typically include either an extensible layer or elastic layer, and at least one surface-bonded nonwoven layer such as a meltblown, spunbond or through-air bonded web. As long as the final transverse direction widths differ as noted with respect to the front and back elastic or extensible panels, a variety of elastic or extensible materials can be used to create the asymmetrical absorbent article.

Furthermore, the front and back panels can be constructed from a monolayer or multilayer elastic film that is capable of being stretched in at least one direction and, desirably, in multiple directions. The front and back panels can be further formed from an elastic nonwoven that has multiple direction stretch capabilities or a laminate of such elastic film and nonwoven materials.

Still further, the front and back panels can be formed from spandex-type materials or two outer layers with a plurality of elastic strands sandwiched therebetween. The elastic strands can be preformed from LYCRA brand fibers/yarns for example. LYCRA is a registered trademark of E. I. Du Pont De Nemours Co., having an office at 1007 Market Street, Wilmington, Del. 19898. The elastic strands can be aligned approximately parallel to one another or be angled or skewed relative to one another. The elastic strands can also be uniformly or randomly spaced apart from one another. The elastic strands can vary in shape, size, configuration, and/or length. The diameter and/or cross-sectional configuration of the elastic strands, the decitex (weight in grams per 10,000 meters of a strand) of the elastic strands, and the tension imparted into the elastic strands can all be varied to suit one's particular product needs. The elastic strands can have a round, semi-circular, square, rectangular, oval or some other geometrical configuration. The elastic strands can overlap, intersect or crisscross at least one other elastic strand. The various ways of positioning, orienting, and adhering the elastic strands to the two outer layers are well known to those skilled in the art. Therefore, the elastic laminate materials for use in this invention may include differentiated zones along their longitudinal direction.

The liquid permeable topsheet layer 100 may be manufactured from any number of conventional materials commonly used as a user-facing surface on an absorbent article. For example, non-limiting examples of such topsheet layer materials include fibrous nonwoven sheet materials, such as spunbond, spunlace, meltblown, and carded web materials (such as thermally bonded carded webs (TBCW), through-air bonded carded webs (TABCW)), fibrous woven sheet materials, apertured film materials, and laminate combinations of the foregoing materials. Further, monolayered or multilayered sheet materials of the foregoing can also be used as the topsheet layer. Particularly, carded web materials may be made from staple, bicomponent fibers as are known in the art. Materials that may be used in the topsheet layer include synthetic fibers, such as polyolefinic materials, and natural fibers, such as cotton spunlace. Such liquid permeable topsheet layers may be apertured, embossed and/or treated with surfactant so as to manipulate the hydrophobicity/hydrophilicity of the topsheet layer(s) in order to enhance fluid transport properties (since the topsheet layer is the first layer to contact body exudates upon excretion from a user's body). The topsheet layer 100 may also be treated so as to impart other properties to the user-facing surface. Examples of additional treatments include application of skin health agents, coloring agents, odor control agents, stain masking agents and the like. Suitable topsheet layer materials include, but are not limited to those described in U.S. Pat. No. 4,397,644 to Matthews et al., U.S. Pat. No. 4,629,643 to Curro et al., U.S. Pat. No. 5,188,625 Van Iten et al., U.S. Pat. No. 5,382,400 to Pike et al., U.S. Pat. No. 5,533,991 to Kirby et al., U.S. Pat. No. 6,410,823 to Daley et al., and United States Publication 2012/0289917 to Abuto et al., each of which is hereby incorporated by reference thereto in its entirety.

The actual absorbent core layer(s) 101 of the absorbent core insert 16 can itself comprise a single layer or multiple layers and these one or more layers can themselves comprise similar or different materials. Highly absorbent core layers often include, but are not limited to, batts or webs containing wood pulp fibers, superabsorbent particles or fibers (also known as SAP or SAM), synthetic wood pulp fibers, synthetic fibers, coformed materials, and combinations thereof. The absorbent core layer may comprise any one of a number of materials and structures, the particular selection of which will vary with the desired loading capacity, flexibility, body fluid to be absorbed and other factors known to those skilled in the art. By way of example, suitable materials and/or structures for the absorbent core layers include, but are not limited to, those described in U.S. Pat. No. 4,610,678 to Weisman et al., U.S. Pat. No. 6,060,636 to Yahiaoui et al., U.S. Pat. No. 6,610,903 to Latimer et al., U.S. Pat. No. 7,358,282 to Krueger et al., and United States patent publication 2010/0174260 to Di Luccio et al., each of which is hereby incorporated by reference thereto in its entirety.

The particular structure and composition of the liquid impermeable backsheet layer 102 may be selected from various known films and/or fabrics with the particular material being selected as appropriate to provide the desired level of liquid barrier, strength, abrasion resistance, tactile properties, aesthetics (such as texture and printability) and so forth. Suitable backsheet layer materials include, but are not limited to, those described in U.S. Pat. No. 4,376,799 to Tusim et al., U.S. Pat. No. 4,578,069 to Whitehead et al., U.S. Pat. No. 5,695,849 to Shawver et al, U.S. Pat. No. 6,075,179 et al. to McCormack et al., and U.S. Pat. No. 6,376,095 to Cheung et al., each of which is hereby incorporated by reference thereto in its entirety. The liquid impermeable backsheet layer may be breathable or non-breathable, as may be desired. In one embodiment, the liquid impermeable backsheet layer is a breathable polyolefinic film having a basis weight of between about 18 and 40 gsm, alternatively between about 20 and 30 gsm, such as of a polyethylene film.

As can be seen from the embodiments described in this disclosure, an absorbent article is now provided in which both user needs for additional physical and emotional comfort are provided. By aligning on a front surface of an absorbent article, inwardly directed bond seams with leg opening vertices from ergonomically shaped openings, an absorbent article can be created which provides both for comfort and aesthetic appeal. Further, by utilizing either differential tension (or machine draw) of two similar elastic panels, or alternatively panels of different elastic functionality (such as dissimilar materials having different retractive power, and alternatively exposed to different tensions in manufacture) to produce such an article, such articles can be produced using CD manufacturing processes.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of making an absorbent article comprising steps of:
    a) producing a first sheet of an elastic material having a longitudinal and transverse direction, with said first sheet being elastic in at least the transverse direction,
    b) producing a second sheet of at least an extensible material having a longitudinal and transverse direction, with said second sheet being at least extensible in at least the transverse direction; and placing said first and second sheets in parallel along their transverse directions on an absorbent article production line;
    c) producing an absorbent core insert having opposing longitudinal direction ends for attachment to said sheets of elastic and at least extensible materials, and opposing lateral side edges extending between said opposing longitudinal direction ends, and bonding the opposing longitudinal direction ends of said absorbent core insert to said sheets of elastic and at least extensible material in a configuration that is perpendicular to said first and second sheet transverse directions while such first and second sheets are under desired levels of tension;
    d) moving said bonded sheets and absorbent core insert through a manufacturing process on said absorbent article production line, along said sheet transverse directions such that differential tensions are applied along said transverse direction to said elastic material compared with said at least extensible material, said tension applied to said elastic material being larger than that applied to said at least extensible material;

e) cutting elongated leg opening shapes along said sheets' longitudinal direction and adjacent said opposing lateral side edges of said absorbent core insert so that the highest point of the cuts will align with side bond seams;

f) bringing the elastic material sheet and the extensible material sheet together to form an absorbent article blank having elongated leg openings with distinct vertex configurations, and subsequently bonding said material sheets to one another alongside bond seams that are generally aligned with said sheets' longitudinal direction and aligned with said vertex configurations in order to form an absorbent article with said elastic sheet and said at least extensible sheet having the same transverse direction width, while maintaining said sheets under their respective tensions;

g) cutting said absorbent article from said absorbent article blank and removing such tension such that said elastic sheet transverse direction width narrows with respect to said at least extensible sheet transverse direction width as a result of differential levels of retraction upon or in said sheets, whereby said bond seams rotate from a lateral-most side location to a forwardly positioned location, off of the lateral-most side edge.

2. The method of claim 1, wherein said first and second sheets of material are both elastic.

3. The method of claim 2, wherein said first and second sheets of material are of different elastic materials.

4. The method of claim 1 wherein said bond seams are constructed of temporarily bonded materials.

5. The method of claim 1 wherein said bond seams are temporary bond seams.

6. A method of making an absorbent article comprising steps of:

a) producing a first sheet of an elastic material having a longitudinal and transverse direction, with said first sheet being elastic in at least the transverse direction, b) producing a second sheet of at least an extensible material having a longitudinal and transverse direction, with said second sheet being at least extensible in at least the transverse direction; and placing said first and second sheets in parallel along their transverse directions on an absorbent article production line;

c) moving said first and second sheets through a manufacturing process on said absorbent article production line, along said sheet transverse directions such that differential tensions are applied along said transverse direction to said first sheet compared with said second sheet, said tension applied to said first sheet being larger than that applied to said second sheet;

d) producing an absorbent core insert having opposing longitudinal direction ends for attachment to said first sheet and second sheet, and opposing lateral side edges extending between said opposing longitudinal direction ends, and bonding the opposing longitudinal direction ends of said absorbent core insert to said first sheet and said second sheet in a configuration that is perpendicular to said first sheet and second sheet transverse directions while such first and second sheets are under desired levels of tension;

e) cutting elongated leg opening shapes along said sheets' longitudinal direction so that the highest point of the cuts will align with bond seams;

f) bringing the first sheet and second sheet together to form an absorbent article blank, and subsequently bonding said material sheets to one another along bond seams that are generally aligned with said sheets' longitudinal direction in order to form an absorbent article with said first sheet and said second sheet having the same transverse direction width, while maintaining said sheets under their respective tensions;

g) cutting said absorbent article from said absorbent article blank and removing such tension such that said first sheet transverse direction width narrows with respect to said second sheet transverse direction width as a result of differential levels of retraction upon or in said sheets, whereby said bond seams rotate from a lateral-most side location to a position location inward of the lateral-most side edge.

* * * * *